(12) United States Patent
Allard et al.

(10) Patent No.: US 7,745,152 B2
(45) Date of Patent: Jun. 29, 2010

(54) METHOD FOR DETERMINING GENOTOXICITY

(75) Inventors: John David Allard, Milpitas, CA (US); Dee Aud, Boulder Creek, CA (US); Guochun Liao, Belmont, CA (US); Gary Allen Peltz, Redwood City, CA (US)

(73) Assignee: Roche Palo Alto LLC, Palo Alto, CA (US)

( * ) Notice: Subject to any disclaimer, the term of this patent is extended or adjusted under 35 U.S.C. 154(b) by 381 days.

(21) Appl. No.: 11/286,216

(22) Filed: Nov. 23, 2005

(65) Prior Publication Data
US 2006/0110768 A1 May 25, 2006

Related U.S. Application Data

(60) Provisional application No. 60/630,672, filed on Nov. 24, 2004.

(51) Int. Cl.
*G01N 33/567* (2006.01)
*C12Q 1/68* (2006.01)
*C12N 15/85* (2006.01)

(52) U.S. Cl. ......................................... 435/7.21; 435/6

(58) Field of Classification Search ....................... None
See application file for complete search history.

(56) References Cited

FOREIGN PATENT DOCUMENTS

WO    WO 99/53092 Y    10/1999
WO    WO 2004/037200 A2    5/2004

OTHER PUBLICATIONS

Van de Peer (2006) Heredity 96:204-205.*
Smith et al. (1997) Nature Biotechnol. 15:1222-1223.*
Skolnick et al. (2000) Trends Biotechnol. 18:34-39.*
Khor et al. (2006) Pharm. Res. 23:1659-1664.*
Collins, Francis S., "Generation and initial analysis of more than 15,000 full-length human and mouse cDNA sequences", *Proc Natl Acad Sci*, Dec. 2002, 99(26):16899-16903.
Hu, Ting, et al, "Identification of a gene expression profile that discriminates indirect-acting genotoxins from direct-acting genotoxins", *Mutation Research*, 2004, 549:5-27 (Elsevier).
Hsieh, Shu-Chen, et al, "Mouse DDA3 gene is a direct transcriptional target of p53 and -73", *Oncogene*, 2002, 21:3050-3057 (Nature).
Liao, Guochun, et al, "In Silico Genetics: Identification of a Functional Element Regulating H2-Eα Gene Expression", *Science*, Oct. 22, 2004, 306:690-695.
Lo, Pang-Kuo, et al, "5'-Heterogeneity of mouse Dda3 transcripts is attributed to differential initiation of transcription and alternative splicing", *Arch Biochem and Biophysics*, 2004, 425-221-232 (Elsevier).
Lo, Pang-Kuo, et al, "Cloning and characterization of human and mouse DDA3 genes", *Biochemica et Biophysica Acta*, 2002, 1579:214-218 (Elsevier).
Puri, Pier Lorenzo, et al, "A mycogenic differentiation checkpoint activated by genotoxic stress", *Nature Genetics*, Dec. 2002, 32:585-593.
Van Delft, J.H.M, et al, "Discrimination of genotoxic from non-genotoxic carcinogens by gene expression profiling", *Carcinogenesis*, 2004, 25(7):1265-1276.
Kawai, J., et al, "Functional annotation of a full-length mouse cDNA collection", *Nature*, Feb. 2001, 409:685-690 (Macmillan).
"Supplementary Figure 1 Distribution of the length of 21,076 insert DNA's; Supplementary Figure 1B Sequence accuracy", *Nature*, 409(6821).
"Supplementary Figure 2 SAP domain containing RIKEN clones", *Nature*, 409(6821).
"Supplementary Figure 3A Phylogenetic tree of the known OATPs and new members; Supplementary Figure 3B Alignment of the amino acid sequences of the known OATPs", *Nature*, 409(6821).
Afanassiev V et al., "Application of yeast cells transformed with GFP expression constructs containing the RAD54 or RNR2 promoter as a test for the genotoxic potential of chemical substances", *Mutation Research*, 2000, 297-308:464.
Ait-Aissa et al., "Induction of the hsp70 gene promoter by various anticancer drugs", 1999, 651-655:13.
Baumstark-Khan, Christa et al., "Application of the Lux-Fluoro test as bioassay for combined genotoxicity and cytotoxicity measurements by means of recombinant *Salmonella typhimurium* TA1535 cells", *Analytica Chimica Acta*, 2001, 23-30:437.
Database EMBL, "*Mus musculus* cDNA clone Image:1746300 5', mRNA sequence", 1998, XP02366987, Database accession No. AI037654.
Grover, Judy et al., "Characterization of the human praline/arginine-rich and leucine-rich repeat protein (PRELP) gene promoter and identification of a repressor element", *Biochemical Journal*, 1998, 77-82:336.
Lo, Pang-Kuo, et al,"Identification of a novel mouse p53 target gene DDA3", *Oncogene*, 1998, 7765-7774:18.
Sohn, Taylor A. et al., "High-throughput measurement of the Tp53 response to anticancer drugs and random compounds using a stably integrated Tp53-responsive luciferase reporter", *Carcinogenesis (Oxford)*, 2002, 949-957:23.

(Continued)

*Primary Examiner*—Michele K Joike
(74) *Attorney, Agent, or Firm*—David J. Chang

(57) ABSTRACT

Methods and reagents for determining the genotoxicity of a compound based on genomic responses to contact therewith are provided.

3 Claims, No Drawings

OTHER PUBLICATIONS

Bains, W., et al., "Cardiac actin is the major actin gene product in skeletal muscle cell differentiation in vitro", *Mol Cell Biol* (1984) vol. 4(8): pp. 1449-1453.

Blau, H.M., et al., "Cytoplasmic Activation of Human Nuclear Genes in Stable Heterocaryons", *Cell* (1983) vol. 32: pp. 1171-1180.

DePonti-Zilli, L., et al., "A 40-base-pair sequence in the 3' end of the β-actin gene regulates β-actin mRNA transcription during myogenesis", *Proc Natl Acad Sci USA* (1988) vol. 85: pp. 1389-1393.

McMahon, D.K., et al., "$C_2C_{12}$ cells: biophysical, biochemical, and immunocytochemical properties", *Am J Physiol* (1994) vol. 266:C1795-C1802.

Parmacek, M.S., et al., "The structure and regulation of expression of the murine fast skeletal troponin C gene", *J Biol Chem* (1990) vol. 265(26):pp. 15970-15976.

Seiler-Tuyns, A., et al., "Expression and regulation of chicken actin genes introduced into mouse myogenic and nonmyogenic cells", *Proc Natl Acad Sci USA* (1984) vol. 81:pp. 2980-2984.

Lo, P., et. al., "Identification of a Novel Mouse p53 Target Gene DDA3," *Oncogene*, 1999, vol. 18, pp. 7765-7774.

Newton, R.K., et. al., "The Utility of DNA Microarrays for Characterizing Genotoxicity," *Environmental Health Perspectives* 2004, vol. 112 (4), pp. 420-422.

Song, K.S., et. al., "Expression of Caveolin-3 in Skeletal, Cardiac, and Smooth Muscle Cells," *J. Biol. Chem.* 1996, vol. 271 (25), pp. 15160-15165.

\* cited by examiner

SEQUENCE LISTING

<160> NUMBER OF SEQ ID NOS: 31

<210> SEQ ID NO 1
<211> LENGTH: 1676
<212> TYPE: DNA
<213> ORGANISM: Mus musculus
<220> FEATURE:
<221> NAME/KEY: CDS
<222> LOCATION: (116)..(1105)

<400> SEQUENCE: 1

```
cgggaactgg gagattgtag aagaaaagct tcctgcgtag actgtgaagc gaggtgggga      60
gtggaaaccg agtgtgcgct ggaggtctaa gccgactcgc ttatgctggc tgagc atg     118
                                                             Met
                                                               1 gag gat ctg aaa gag gat atc aag ttc att gtg gac gag acc ttg gac       166
Glu Asp Leu Lys Glu Asp Ile Lys Phe Ile Val Asp Glu Thr Leu Asp
        5                  10                  15 ttc gga ggg ctg tct cca tct gac agt cat gag gaa gaa gac ata aca       214
Phe Gly Gly Leu Ser Pro Ser Asp Ser His Glu Glu Glu Asp Ile Thr
20                  25                  30 gta tta gtg agt cca gag aaa cca ctt cga cgg ggc ctc gcc cat cgg       262
Val Leu Val Ser Pro Glu Lys Pro Leu Arg Arg Gly Leu Ala His Arg
    35                  40                  45 agt aac cca aat gaa gta gct ccc gcc ctc cag ggt gtg cgg ttt agc       310
Ser Asn Pro Asn Glu Val Ala Pro Ala Leu Gln Gly Val Arg Phe Ser
50                  55                  60                  65 ttg ggc ccg ctc agc cca gag aag ctg gaa gag att ctt gat gaa gcc       358
Leu Gly Pro Leu Ser Pro Glu Lys Leu Glu Glu Ile Leu Asp Glu Ala
                70                  75                  80 aac cgc ctg gcg gct cag ctg gag gag tgt gcc ctg aaa gat cgg gag       406
Asn Arg Leu Ala Ala Gln Leu Glu Glu Cys Ala Leu Lys Asp Arg Glu
            85                  90                  95 agg gct ggt aca ggc cct gga agg ccc agc ccc aga ggg aaa ccc agt       454
Arg Ala Gly Thr Gly Pro Gly Arg Pro Ser Pro Arg Gly Lys Pro Ser
        100                 105                 110 cct cgg cgg gag acc ttc gtc ctg aag gat agc cct gtc cga gat ctg       502
Pro Arg Arg Glu Thr Phe Val Leu Lys Asp Ser Pro Val Arg Asp Leu
    115                 120                 125 ctg ccc acc gtg agt tct tgg agc acc cca cct cca agc agc cta gct       550
Leu Pro Thr Val Ser Ser Trp Ser Thr Pro Pro Pro Ser Ser Leu Ala
130                 135                 140                 145 ggg ctc cgg agc agt gat aaa aag ggg tca gcc agg gct gtc cgg gtg       598
Gly Leu Arg Ser Ser Asp Lys Lys Gly Ser Ala Arg Ala Val Arg Val
                150                 155                 160 gca tcc gga aag aag ccc tcc agc ata aag aag gaa tca ccc act tgc       646
Ala Ser Gly Lys Lys Pro Ser Ser Ile Lys Lys Glu Ser Pro Thr Cys
            165                 170                 175 aat ctg ttc cct gca tcc aaa agc ccg ggg cgc tct cct ctt gca caa       694
Asn Leu Phe Pro Ala Ser Lys Ser Pro Gly Arg Ser Pro Leu Ala Gln
        180                 185                 190 cca att ctt cca cct cgg cgg aaa act ggg ttc ggt gcc cgg aca aca       742
Pro Ile Leu Pro Pro Arg Arg Lys Thr Gly Phe Gly Ala Arg Thr Thr
    195                 200                 205 gca agc cca cca att cct gtc aga cca gtt cca cag tcc tca gct agc       790
Ala Ser Pro Pro Ile Pro Val Arg Pro Val Pro Gln Ser Ser Ala Ser
210                 215                 220                 225 aac tcc caa tgt tca tcc cgg ctc cag gga gca gct gtc aag tct tcc       838
Asn Ser Gln Cys Ser Ser Arg Leu Gln Gly Ala Ala Val Lys Ser Ser
                230                 235                 240
```

```
agt cga ctc cct gtc cct tca gcc atc ccc aag cct gcc acc cga gtg    886
Ser Arg Leu Pro Val Pro Ser Ala Ile Pro Lys Pro Ala Thr Arg Val
        245                 250                 255 cca ctc att ggg cgg agt cta cca cct gga aaa ggt gcc cta gct cca    934
Pro Leu Ile Gly Arg Ser Leu Pro Pro Gly Lys Gly Ala Leu Ala Pro
    260                 265                 270 gat tct ctc tca act cag aaa ggg cat cca agc gcc ata ggg cac aga    982
Asp Ser Leu Ser Thr Gln Lys Gly His Pro Ser Ala Ile Gly His Arg
275                 280                 285 gcc tct gtt tcc cag aaa aca aac ctt cca acc acc agt gcg gct cga   1030
Ala Ser Val Ser Gln Lys Thr Asn Leu Pro Thr Thr Ser Ala Ala Arg
290                 295                 300                 305 ggc agg acc acc agt gcc gct cga ggc agg gcg cag ccc ctc agg aaa   1078
Gly Arg Thr Thr Ser Ala Ala Arg Gly Arg Ala Gln Pro Leu Arg Lys
            310                 315                 320 gct gca gtc cct gga ccg act agg taa gaagagcacg tcagcaaaca         1125
Ala Ala Val Pro Gly Pro Thr Arg
                325 aagactcaat agcaagccac taccatctta gccatcaaag tctggactct cctctgccag  1185 tggtccctaa ctccagtagc tctgtgccca gagatgggag gaagagatgc ctccagggct  1245 gacctctgaa gtagagacta tgggggatcg ggtgccttga gcttgagggg actcaacccc  1305 accctaccct gccctgaaag aagaagagag gggcagaggt catctgcccg tggagaaact  1365 cacaaacaaa ataataaatg caggcagagt gacctatctg tctccttcca tcttgtggtc  1425 aggactagag agcttgatct ctaccacgg ttcactggcc attcccatat gagcggcctt   1485 aggagcccgc cggctcagtt ctctatgaca tgtcttcctg actggatact ggtctgtttg   1545 gaaaggccag gaggacagct gatgtacaga acttgtttcc tatgaattct ttgacttctc   1605 acaggtcaat cagttataag cttactcaca tcttcatatt ttttcttaaa taaatgaatt   1665 aaaaaaaaaa a                                                      1676

<210> SEQ ID NO 2
<211> LENGTH: 329
<212> TYPE: PRT
<213> ORGANISM: Mus musculus

<400> SEQUENCE: 2

Met Glu Asp Leu Lys Glu Asp Ile Lys Phe Ile Val Asp Glu Thr Leu
1               5                   10                  15

Asp Phe Gly Gly Leu Ser Pro Ser Asp Ser His Glu Glu Glu Asp Ile
            20                  25                  30

Thr Val Leu Val Ser Pro Glu Lys Pro Leu Arg Arg Gly Leu Ala His
        35                  40                  45

Arg Ser Asn Pro Asn Glu Val Ala Pro Ala Leu Gln Gly Val Arg Phe
    50                  55                  60

Ser Leu Gly Pro Leu Ser Pro Glu Lys Leu Glu Glu Ile Leu Asp Glu
65                  70                  75                  80

Ala Asn Arg Leu Ala Ala Gln Leu Glu Glu Cys Ala Leu Lys Asp Arg
                85                  90                  95

Glu Arg Ala Gly Thr Gly Pro Gly Arg Pro Ser Pro Arg Gly Lys Pro
            100                 105                 110

Ser Pro Arg Arg Glu Thr Phe Val Leu Lys Asp Ser Pro Val Arg Asp
        115                 120                 125

Leu Leu Pro Thr Val Ser Ser Trp Ser Thr Pro Pro Ser Ser Leu
    130                 135                 140
```

-continued

```
Ala Gly Leu Arg Ser Ser Asp Lys Lys Gly Ser Ala Arg Ala Val Arg
145                 150                 155                 160

Val Ala Ser Gly Lys Lys Pro Ser Ser Ile Lys Lys Glu Ser Pro Thr
                165                 170                 175

Cys Asn Leu Phe Pro Ala Ser Lys Ser Pro Gly Arg Ser Pro Leu Ala
            180                 185                 190

Gln Pro Ile Leu Pro Pro Arg Arg Lys Thr Gly Phe Gly Ala Arg Thr
        195                 200                 205

Thr Ala Ser Pro Pro Ile Pro Val Arg Pro Val Pro Gln Ser Ser Ala
    210                 215                 220

Ser Asn Ser Gln Cys Ser Ser Arg Leu Gln Gly Ala Ala Val Lys Ser
225                 230                 235                 240

Ser Ser Arg Leu Pro Val Pro Ser Ala Ile Pro Lys Pro Ala Thr Arg
                245                 250                 255

Val Pro Leu Ile Gly Arg Ser Leu Pro Pro Lys Gly Ala Leu Ala
            260                 265                 270

Pro Asp Ser Leu Ser Thr Gln Lys Gly His Pro Ser Ala Ile Gly His
        275                 280                 285

Arg Ala Ser Val Ser Gln Lys Thr Asn Leu Pro Thr Thr Ser Ala Ala
    290                 295                 300

Arg Gly Arg Thr Thr Ser Ala Ala Arg Gly Arg Ala Gln Pro Leu Arg
305                 310                 315                 320

Lys Ala Ala Val Pro Gly Pro Thr Arg
                325
```

```
<210> SEQ ID NO 3
<211> LENGTH: 1572
<212> TYPE: DNA
<213> ORGANISM: Homo sapiens
<220> FEATURE:
<221> NAME/KEY: CDS
<222> LOCATION: (76)..(1008)

<400> SEQUENCE: 3
aagataaggc ggcgcgggaa gtggacacag ggtgggctgg agatctaact ggactctcgc      60
tcctgctggc tggac atg gag gat ttg gag gaa gat gta agg ttt att gtg     111
                Met Glu Asp Leu Glu Glu Asp Val Arg Phe Ile Val
                  1               5                  10 gat gag acc ttg gac ttt ggg ggg ctg tca cca tct gac agc cgt gag     159
Asp Glu Thr Leu Asp Phe Gly Gly Leu Ser Pro Ser Asp Ser Arg Glu
            15                  20                  25 gag gaa gac ata aca gtg ttg gtg act cca gag aaa cca ctt cga cgg     207
Glu Glu Asp Ile Thr Val Leu Val Thr Pro Glu Lys Pro Leu Arg Arg
        30                  35                  40 ggc ctc tcc cac cga agt gac cca aat gca gtg gca cct gcc ccc cag     255
Gly Leu Ser His Arg Ser Asp Pro Asn Ala Val Ala Pro Ala Pro Gln
45                  50                  55                  60 ggt gtg agg ctc agc cta ggc ccc ctc agt cca gag aag ctg gag gag     303
Gly Val Arg Leu Ser Leu Gly Pro Leu Ser Pro Glu Lys Leu Glu Glu
                65                  70                  75 atc ctc gat gag gcc aac cgg ctg gcc gct cag ctg gag cag tgt gcc     351
Ile Leu Asp Glu Ala Asn Arg Leu Ala Ala Gln Leu Glu Gln Cys Ala
            80                  85                  90 ctg cag gat cgg gag agc gca ggc gag ggc ctg ggg cct cgc cga gtg     399
Leu Gln Asp Arg Glu Ser Ala Gly Glu Gly Leu Gly Pro Arg Arg Val
        95                  100                 105 aag ccc agt cct cgg cgg gag acc ttt gtg ctg aag gat agt cct gtc     447
Lys Pro Ser Pro Arg Arg Glu Thr Phe Val Leu Lys Asp Ser Pro Val
```

-continued

```
       110                 115                 120
cga gac ctg ctg ccc act gtg aac tct ttg acg cgg agc acc ccc tcc    495
Arg Asp Leu Leu Pro Thr Val Asn Ser Leu Thr Arg Ser Thr Pro Ser
125                 130                 135                 140 cca agc agc ctg acg cct cga ctc cgg agt aat gat agg aag ggg tca    543
Pro Ser Ser Leu Thr Pro Arg Leu Arg Ser Asn Asp Arg Lys Gly Ser
                145                 150                 155 gtc agg gct ctc cgg gct aca tct gga aag agg ccc tcc aac atg aag    591
Val Arg Ala Leu Arg Ala Thr Ser Gly Lys Arg Pro Ser Asn Met Lys
            160                 165                 170 agg gag tca ccc act tgc aat ctg ttc cct gca tcc aaa agc cca gca    639
Arg Glu Ser Pro Thr Cys Asn Leu Phe Pro Ala Ser Lys Ser Pro Ala
        175                 180                 185 tct tct cct ctt acc cga tcg act ccc cca gtc cgg ggg aga gcc ggg    687
Ser Ser Pro Leu Thr Arg Ser Thr Pro Pro Val Arg Gly Arg Ala Gly
    190                 195                 200 ccc agt ggg aga gca gca gcc agt gag gag acc aga gca gcc aag ttg    735
Pro Ser Gly Arg Ala Ala Ala Ser Glu Glu Thr Arg Ala Ala Lys Leu
205                 210                 215                 220 cgg gcc tgc cag ccg aat gcc act cac cag ccg gag tgt gcc acc tgg    783
Arg Ala Cys Gln Pro Asn Ala Thr His Gln Pro Glu Cys Ala Thr Trp
                225                 230                 235 cag agg tgc cct acc tcc gga ttc tct gtc aac tcg aaa agg gct tcc    831
Gln Arg Cys Pro Thr Ser Gly Phe Ser Val Asn Ser Lys Arg Ala Ser
            240                 245                 250 aag acc aag cac tgc agg aca cag agt gcg gga aag tgg aca caa ggt    879
Lys Thr Lys His Cys Arg Thr Gln Ser Ala Gly Lys Trp Thr Gln Gly
        255                 260                 265 tcc tgt ttc cca gcg act aaa tct tcc tgt cat ggg tgc cac tcg cag    927
Ser Cys Phe Pro Ala Thr Lys Ser Ser Cys His Gly Cys His Ser Gln
    270                 275                 280 caa tct gca gcc ccc cag gaa agt ggc agt ccc agg acc tac cag gta    975
Gln Ser Ala Ala Pro Gln Glu Ser Gly Ser Pro Arg Thr Tyr Gln Val
285                 290                 295                 300 aag aga tca gga cag caa gca aga ctt cag tag caaaccacta cagtcagtac   1028
Lys Arg Ser Gly Gln Gln Ala Arg Leu Gln
                305                 310 ctggactcgc tctacccag cagaccctga ctccagcaga ttctggccca gggacaggag    1088
gaagagatgc caccagggct ggtctcccag gagtagagac catgggaaat ggggtggatt    1148
aggattgagc tggagaagac ttaaactctc tgggttgaaa gaagattagg ggaaaagagg    1208
tcaccttcca gcagtgaaat gaacaaatag aagatgagaa gtacaggcaa gtggtttgtc    1268
tttatccacc cccactgttg tggtcagccc cagagaattt tatcttcttc cttggcattg    1328
gttcactgga catttccacg tgagcggcct ccgtagctaa cctccctgcc ctctgaggag    1388
ccatcttcct gaatcgcatt ctctactgga ctctggcctg cttggagagg tggcagcagg    1448
cacctggtct tcagaaattg tttcctgtga attctgtgac tcctaatagg ccagtttgtg    1508
ataagcttac tctatgagtc ttcatttttc taaaataaag tgaatgtatt tttatattct    1568
ctgt                                                                 1572

<210> SEQ ID NO 4
<211> LENGTH: 310
<212> TYPE: PRT
<213> ORGANISM: Homo sapiens

<400> SEQUENCE: 4

Met Glu Asp Leu Glu Glu Asp Val Arg Phe Ile Val Asp Glu Thr Leu
```

```
                    1               5                  10                 15
Asp Phe Gly Gly Leu Ser Pro Ser Asp Ser Arg Glu Glu Glu Asp Ile
                20                  25                 30

Thr Val Leu Val Thr Pro Glu Lys Pro Leu Arg Arg Gly Leu Ser His
            35                  40                 45

Arg Ser Asp Pro Asn Ala Val Ala Pro Ala Pro Gln Gly Val Arg Leu
        50                  55                 60

Ser Leu Gly Pro Leu Ser Pro Glu Lys Leu Glu Glu Ile Leu Asp Glu
65                  70                  75                 80

Ala Asn Arg Leu Ala Ala Gln Leu Glu Gln Cys Ala Leu Gln Asp Arg
                85                  90                 95

Glu Ser Ala Gly Glu Gly Leu Gly Pro Arg Arg Val Lys Pro Ser Pro
            100                 105                110

Arg Arg Glu Thr Phe Val Leu Lys Asp Ser Pro Val Arg Asp Leu Leu
        115                 120                 125

Pro Thr Val Asn Ser Leu Thr Arg Ser Thr Pro Ser Pro Ser Ser Leu
    130                 135                 140

Thr Pro Arg Leu Arg Ser Asn Asp Arg Lys Gly Ser Val Arg Ala Leu
145                 150                 155                160

Arg Ala Thr Ser Gly Lys Arg Pro Ser Asn Met Lys Arg Glu Ser Pro
                165                 170                175

Thr Cys Asn Leu Phe Pro Ala Ser Lys Ser Pro Ala Ser Ser Pro Leu
            180                 185                190

Thr Arg Ser Thr Pro Pro Val Arg Gly Arg Ala Gly Pro Ser Gly Arg
        195                 200                 205

Ala Ala Ala Ser Glu Glu Thr Arg Ala Ala Lys Leu Arg Ala Cys Gln
    210                 215                 220

Pro Asn Ala Thr His Gln Pro Glu Cys Ala Thr Trp Gln Arg Cys Pro
225                 230                 235                240

Thr Ser Gly Phe Ser Val Asn Ser Lys Arg Ala Ser Lys Thr Lys His
                245                 250                255

Cys Arg Thr Gln Ser Ala Gly Lys Trp Thr Gln Gly Ser Cys Phe Pro
            260                 265                270

Ala Thr Lys Ser Ser Cys His Gly Cys His Ser Gln Gln Ser Ala Ala
        275                 280                 285

Pro Gln Glu Ser Gly Ser Pro Arg Thr Tyr Gln Val Lys Arg Ser Gly
    290                 295                 300

Gln Gln Ala Arg Leu Gln
305                 310

<210> SEQ ID NO 5
<211> LENGTH: 808
<212> TYPE: DNA
<213> ORGANISM: Mus musculus
<220> FEATURE:
<221> NAME/KEY: CDS
<222> LOCATION: (109)..(615)

<400> SEQUENCE: 5
agatctacgg aagaagaaac acaggcattc cggtggtggc agttaccaac aggacggttc      60
tccggtaggg gcgggacgcc agagctaagg aaagcgtcct gagtcacc atg gaa acg     117
                                                    Met Glu Thr
                                                      1 ggg ccc aga ggc tgt cct agc ggc agg aag gaa tcc cag gaa atc tgc     165
Gly Pro Arg Gly Cys Pro Ser Gly Arg Lys Glu Ser Gln Glu Ile Cys
      5                  10                  15
```

```
tcc cct gga tta ctg gtg ttc acc ggc tgc tct gag cag gat gcc aat       213
Ser Pro Gly Leu Leu Val Phe Thr Gly Cys Ser Glu Gln Asp Ala Asn
 20                  25                  30                  35 ttg gct aag cag ttt tgg ctc ggg gcg tcc atg tac ccc act acc gaa       261
Leu Ala Lys Gln Phe Trp Leu Gly Ala Ser Met Tyr Pro Thr Thr Glu
                 40                  45                  50 tct cag ctc gtg ctg acc cga ggc agc agt cag agg cta ccg gtg gcg       309
Ser Gln Leu Val Leu Thr Arg Gly Ser Ser Gln Arg Leu Pro Val Ala
             55                  60                  65 cgg aac tct aaa gtc gtt ctg aga gag aaa agt tct gtc cag ccc ttt       357
Arg Asn Ser Lys Val Val Leu Arg Glu Lys Ser Ser Val Gln Pro Phe
         70                  75                  80 ccc ttt gat cag gac aag gat gca att atc ttt gct aaa gcc caa agg       405
Pro Phe Asp Gln Asp Lys Asp Ala Ile Ile Phe Ala Lys Ala Gln Arg
     85                  90                  95 att cag gaa tct gaa gag aga gca aag tat ctc caa aag gcc aaa acg       453
Ile Gln Glu Ser Glu Glu Arg Ala Lys Tyr Leu Gln Lys Ala Lys Thr
100                 105                 110                 115 cga gat gag att ctc caa ctt tta agg aaa caa aga gaa gaa agg atc       501
Arg Asp Glu Ile Leu Gln Leu Leu Arg Lys Gln Arg Glu Glu Arg Ile
                    120                 125                 130 tcg aaa gaa ctg att tca tta cct tat aaa cct aag gac aaa gtg ccc       549
Ser Lys Glu Leu Ile Ser Leu Pro Tyr Lys Pro Lys Asp Lys Val Pro
                135                 140                 145 aaa tca aag gaa gtt tta tca gag tca ggc cta agg gac caa gaa gaa       597
Lys Ser Lys Glu Val Leu Ser Glu Ser Gly Leu Arg Asp Gln Glu Glu
            150                 155                 160 gtc aaa gcc ttg gaa tga tttgattgac atatggtatc gactgactga              645
Val Lys Ala Leu Glu
        165 tatgtgttca cccttacagc aagttatgct tacagcagga tcagtaggtt aaagatgtgc     705 agacttccgg gaatttgaca gttactgaac attcatgtta aaatagacta aataaattt      765 tcagaattca accaaaaaaa aaaaaaaaaa aaaaaaaaaa aaa                        808

<210> SEQ ID NO 6
<211> LENGTH: 168
<212> TYPE: PRT
<213> ORGANISM: Mus musculus

<400> SEQUENCE: 6

Met Glu Thr Gly Pro Arg Gly Cys Pro Ser Gly Arg Lys Glu Ser Gln
  1               5                  10                  15

Glu Ile Cys Ser Pro Gly Leu Leu Val Phe Thr Gly Cys Ser Glu Gln
                 20                  25                  30

Asp Ala Asn Leu Ala Lys Gln Phe Trp Leu Gly Ala Ser Met Tyr Pro
             35                  40                  45

Thr Thr Glu Ser Gln Leu Val Leu Thr Arg Gly Ser Ser Gln Arg Leu
 50                  55                  60

Pro Val Ala Arg Asn Ser Lys Val Val Leu Arg Glu Lys Ser Ser Val
 65                  70                  75                  80

Gln Pro Phe Pro Phe Asp Gln Asp Lys Asp Ala Ile Ile Phe Ala Lys
                 85                  90                  95

Ala Gln Arg Ile Gln Glu Ser Glu Glu Arg Ala Lys Tyr Leu Gln Lys
            100                 105                 110

Ala Lys Thr Arg Asp Glu Ile Leu Gln Leu Leu Arg Lys Gln Arg Glu
        115                 120                 125
```

```
Glu Arg Ile Ser Lys Glu Leu Ile Ser Leu Pro Tyr Lys Pro Lys Asp
        130                 135                 140

Lys Val Pro Lys Ser Lys Glu Val Leu Ser Glu Ser Gly Leu Arg Asp
145                 150                 155                 160

Gln Glu Glu Val Lys Ala Leu Glu
                165

<210> SEQ ID NO 7
<211> LENGTH: 691
<212> TYPE: DNA
<213> ORGANISM: Homo sapiens
<220> FEATURE:
<221> NAME/KEY: CDS
<222> LOCATION: (1)..(489)

<400> SEQUENCE: 7 atg gaa acg gga ccc agc gaa gaa cct agc ggc cga aaa gag tcc cag      48
Met Glu Thr Gly Pro Ser Glu Glu Pro Ser Gly Arg Lys Glu Ser Gln
1               5                   10                  15 gaa atg tgc ccc ccg gga tta ctg gta ttt gct ggc tcg tcg gaa caa      96
Glu Met Cys Pro Pro Gly Leu Leu Val Phe Ala Gly Ser Ser Glu Gln
            20                  25                  30 gat gcc aac ttg gct aag cag ttc tgg atc tcg gcg tcg atg tat ccc     144
Asp Ala Asn Leu Ala Lys Gln Phe Trp Ile Ser Ala Ser Met Tyr Pro
        35                  40                  45 cct agc gaa tct cag ctg gtg ctg cgc aga gac agc agt cag cgt ctg     192
Pro Ser Glu Ser Gln Leu Val Leu Arg Arg Asp Ser Ser Gln Arg Leu
    50                  55                  60 ccg gtg gcg cgg ccc agg agg agc aga gga ttg aat ttg act tta ttc     240
Pro Val Ala Arg Pro Arg Arg Ser Arg Gly Leu Asn Leu Thr Leu Phe
65                  70                  75                  80 cct cta gaa aat aga gac atc ttt gcc gaa gcc cta aag ata cag gaa     288
Pro Leu Glu Asn Arg Asp Ile Phe Ala Glu Ala Leu Lys Ile Gln Glu
                85                  90                  95 tct gag gag aaa gta aag tat ctc caa aag gct aaa aca aga gaa gag     336
Ser Glu Glu Lys Val Lys Tyr Leu Gln Lys Ala Lys Thr Arg Glu Glu
            100                 105                 110 att ctc caa ctc tta aga aaa caa aga gaa gaa agg atc tcg aaa gaa     384
Ile Leu Gln Leu Leu Arg Lys Gln Arg Glu Glu Arg Ile Ser Lys Glu
        115                 120                 125 ctg att tcc ctt ccg tat aaa cca aaa gcc aaa gaa cac aaa gca aag     432
Leu Ile Ser Leu Pro Tyr Lys Pro Lys Ala Lys Glu His Lys Ala Lys
    130                 135                 140 aaa gtg gta tca gag tca gat aaa gag gac caa gaa gaa gtc aaa act     480
Lys Val Val Ser Glu Ser Asp Lys Glu Asp Gln Glu Glu Val Lys Thr
145                 150                 155                 160 ttg gac taa tttgcttgac acatggcaga ggatggctca cttatacctt             529
Leu Asp cactttggaa acaaccttct cttagatcag gatcattgag atcactggca acattatagt   589
agacaaagaa atacaagtta aatacgcaga cttccaggaa ttttaccagt tagtgagtac   649
ttgtgttaaa ataaagaaat aaaggttaaa tatgcaggct tc                      691

<210> SEQ ID NO 8
<211> LENGTH: 162
<212> TYPE: PRT
<213> ORGANISM: Homo sapiens

<400> SEQUENCE: 8

Met Glu Thr Gly Pro Ser Glu Glu Pro Ser Gly Arg Lys Glu Ser Gln
1               5                   10                  15
```

```
Glu Met Cys Pro Pro Gly Leu Leu Val Phe Ala Gly Ser Ser Glu Gln
            20                  25                  30

Asp Ala Asn Leu Ala Lys Gln Phe Trp Ile Ser Ala Ser Met Tyr Pro
        35                  40                  45

Pro Ser Glu Ser Gln Leu Val Leu Arg Arg Asp Ser Ser Gln Arg Leu
    50                  55                  60

Pro Val Ala Arg Pro Arg Ser Arg Gly Leu Asn Leu Thr Leu Phe
65                  70                  75                  80

Pro Leu Glu Asn Arg Asp Ile Phe Ala Glu Ala Leu Lys Ile Gln Glu
                85                  90                  95

Ser Glu Glu Lys Val Lys Tyr Leu Gln Lys Ala Lys Thr Arg Glu Glu
            100                 105                 110

Ile Leu Gln Leu Leu Arg Lys Gln Arg Glu Glu Arg Ile Ser Lys Glu
        115                 120                 125

Leu Ile Ser Leu Pro Tyr Lys Pro Lys Ala Lys Glu His Lys Ala Lys
    130                 135                 140

Lys Val Val Ser Glu Ser Asp Lys Glu Asp Gln Glu Glu Val Lys Thr
145                 150                 155                 160

Leu Asp

<210> SEQ ID NO 9
<211> LENGTH: 336
<212> TYPE: DNA
<213> ORGANISM: Rattus norvegicus
<220> FEATURE:
<221> NAME/KEY: CDS
<222> LOCATION: (1)..(336)

<400> SEQUENCE: 9 atg gaa acg ggg ccc aga ggc tgt cct agc gtc agg aag gaa ccg cag     48
Met Glu Thr Gly Pro Arg Gly Cys Pro Ser Val Arg Lys Glu Pro Gln
1               5                   10                  15 gaa atc tgc tcc cct gga tta ctt gtg ttc act ggc tgc tct gag cag     96
Glu Ile Cys Ser Pro Gly Leu Leu Val Phe Thr Gly Cys Ser Glu Gln
            20                  25                  30 gat gcc aac ttg gct aag cag ttt tgg ctc ggg gcg tcc atg tac ccc    144
Asp Ala Asn Leu Ala Lys Gln Phe Trp Leu Gly Ala Ser Met Tyr Pro
        35                  40                  45 act acc gaa tct cag ctg gtg ctg acc cga ggc agt agt cag agg cta    192
Thr Thr Glu Ser Gln Leu Val Leu Thr Arg Gly Ser Ser Gln Arg Leu
    50                  55                  60 ccg gtg gcg cgg aac tct aaa gtc ctt gtg agc gag aga aat tct gtc    240
Pro Val Ala Arg Asn Ser Lys Val Leu Val Ser Glu Arg Asn Ser Val
65                  70                  75                  80 aag ccc ttt ccc ttt gat cac aac aag gaa gag att ctc ttt gct aaa    288
Lys Pro Phe Pro Phe Asp His Asn Lys Glu Glu Ile Leu Phe Ala Lys
                85                  90                  95 gcc caa aag gtt cag gaa tct gaa gag aaa gca aac tat ctc caa aag    336
Ala Gln Lys Val Gln Glu Ser Glu Glu Lys Ala Asn Tyr Leu Gln Lys
            100                 105                 110

<210> SEQ ID NO 10
<211> LENGTH: 112
<212> TYPE: PRT
<213> ORGANISM: Rattus norvegicus

<400> SEQUENCE: 10

Met Glu Thr Gly Pro Arg Gly Cys Pro Ser Val Arg Lys Glu Pro Gln
1               5                   10                  15
```

```
Glu Ile Cys Ser Pro Gly Leu Leu Val Phe Thr Gly Cys Ser Glu Gln
             20                  25                  30

Asp Ala Asn Leu Ala Lys Gln Phe Trp Leu Gly Ala Ser Met Tyr Pro
         35                  40                  45

Thr Thr Glu Ser Gln Leu Val Leu Thr Arg Gly Ser Ser Gln Arg Leu
 50                  55                  60

Pro Val Ala Arg Asn Ser Lys Val Leu Val Ser Glu Arg Asn Ser Val
65                  70                  75                  80

Lys Pro Phe Pro Phe Asp His Asn Lys Glu Glu Ile Leu Phe Ala Lys
                 85                  90                  95

Ala Gln Lys Val Gln Glu Ser Glu Gly Lys Ala Asn Tyr Leu Gln Lys
            100                 105                 110

<210> SEQ ID NO 11
<211> LENGTH: 361
<212> TYPE: DNA
<213> ORGANISM: Danio rerio
<220> FEATURE:
<221> NAME/KEY: CDS
<222> LOCATION: (1)..(360)

<400> SEQUENCE: 11 atg agt gaa gaa cta gac gaa gag gtt tta gac ggt ctt aca gaa gtc        48
Met Ser Glu Glu Leu Asp Glu Glu Val Leu Asp Gly Leu Thr Glu Val
 1               5                  10                  15 gaa aaa ttg tat aca gtt ttt cat gga gcg tcg caa gaa gat gtg gcg        96
Glu Lys Leu Tyr Thr Val Phe His Gly Ala Ser Gln Glu Asp Val Ala
             20                  25                  30 tac gca aag ctt ttc tgg aat tct ctt tct ctt caa cca ccg ata gag       144
Tyr Ala Lys Leu Phe Trp Asn Ser Leu Ser Leu Gln Pro Pro Ile Glu
         35                  40                  45 tcc cgt ctc gtt tct tcc gac atc aga cag cgc tta aaa gtt gcg aaa       192
Ser Arg Leu Val Ser Ser Asp Ile Arg Gln Arg Leu Lys Val Ala Lys
 50                  55                  60 acc ccg aac aag agg aat gag gaa atc caa caa gat gct tac ctg agg       240
Thr Pro Asn Lys Arg Asn Glu Glu Ile Gln Gln Asp Ala Tyr Leu Arg
65                  70                  75                  80 caa aag cag gag gag aag cag aga tac atg gag atg gca aaa aat cga       288
Gln Lys Gln Glu Glu Lys Gln Arg Tyr Met Glu Met Ala Lys Asn Arg
                 85                  90                  95 gac cag att atc gcc ctt ctg aaa aag cag agg gat gaa cga att aag       336
Asp Gln Ile Ile Ala Leu Leu Lys Lys Gln Arg Asp Glu Arg Ile Lys
            100                 105                 110 att tca gtg gat aac cgg aca ggt g                                     361
Ile Ser Val Asp Asn Arg Thr Gly
        115                 120

<210> SEQ ID NO 12
<211> LENGTH: 120
<212> TYPE: PRT
<213> ORGANISM: Danio rerio

<400> SEQUENCE: 12

Met Ser Glu Glu Leu Asp Glu Glu Val Leu Asp Gly Leu Thr Glu Val
 1               5                  10                  15

Glu Lys Leu Tyr Thr Val Phe His Gly Ala Ser Gln Glu Asp Val Ala
             20                  25                  30

Tyr Ala Lys Leu Phe Trp Asn Ser Leu Ser Leu Gln Pro Pro Ile Glu
         35                  40                  45
```

```
Ser Arg Leu Val Ser Ser Asp Ile Arg Gln Arg Leu Lys Val Ala Lys
    50                  55                  60

Thr Pro Asn Lys Arg Asn Glu Glu Ile Gln Gln Asp Ala Tyr Leu Arg
65                  70                  75                  80

Gln Lys Gln Glu Glu Lys Gln Arg Tyr Met Glu Met Ala Lys Asn Arg
                85                  90                  95

Asp Gln Ile Ile Ala Leu Leu Lys Lys Gln Arg Asp Glu Arg Ile Lys
            100                 105                 110

Ile Ser Val Asp Asn Arg Thr Gly
        115                 120

<210> SEQ ID NO 13
<211> LENGTH: 361
<212> TYPE: DNA
<213> ORGANISM: Danio rerio
<220> FEATURE:
<221> NAME/KEY: CDS
<222> LOCATION: (1)..(360)

<400> SEQUENCE: 13 atg att gaa gaa cta gac gaa gag gtt tta gac ggt ctt aca gaa gtc      48
Met Ile Glu Glu Leu Asp Glu Glu Val Leu Asp Gly Leu Thr Glu Val
1               5                   10                  15 gaa aaa ttg tat aca gtt ttt cat gga gcg tcg caa gaa gat gtg gcg      96
Glu Lys Leu Tyr Thr Val Phe His Gly Ala Ser Gln Glu Asp Val Ala
            20                  25                  30 tac gca aag ctt ttc tgg aat tct ctt tct ctt caa cca ccg ata gag     144
Tyr Ala Lys Leu Phe Trp Asn Ser Leu Ser Leu Gln Pro Pro Ile Glu
        35                  40                  45 tcc cgt ctc gtt tct tcc gac atc aga cag cgc tta aaa gtt gcg aaa     192
Ser Arg Leu Val Ser Ser Asp Ile Arg Gln Arg Leu Lys Val Ala Lys
    50                  55                  60 acc ccg aac aag agg aat gag gaa atc caa caa gat gct tac ctg agg     240
Thr Pro Asn Lys Arg Asn Glu Glu Ile Gln Gln Asp Ala Tyr Leu Arg
65                  70                  75                  80 caa aag cag gag gag aag cag aga tac atg gag atg gca aaa aat cga     288
Gln Lys Gln Glu Glu Lys Gln Arg Tyr Met Glu Met Ala Lys Asn Arg
                85                  90                  95 gac cag att atc gcc ctt ctg aaa aag cag agg gat gaa cga att aag     336
Asp Gln Ile Ile Ala Leu Leu Lys Lys Gln Arg Asp Glu Arg Ile Lys
            100                 105                 110 att tca gtg gat aac cgg aca ggt g                                   361
Ile Ser Val Asp Asn Arg Thr Gly
        115                 120

<210> SEQ ID NO 14
<211> LENGTH: 120
<212> TYPE: PRT
<213> ORGANISM: Danio rerio

<400> SEQUENCE: 14

Met Ile Glu Glu Leu Asp Glu Glu Val Leu Asp Gly Leu Thr Glu Val
1               5                   10                  15

Glu Lys Leu Tyr Thr Val Phe His Gly Ala Ser Gln Glu Asp Val Ala
            20                  25                  30

Tyr Ala Lys Leu Phe Trp Asn Ser Leu Ser Leu Gln Pro Pro Ile Glu
        35                  40                  45

Ser Arg Leu Val Ser Ser Asp Ile Arg Gln Arg Leu Lys Val Ala Lys
    50                  55                  60

Thr Pro Asn Lys Arg Asn Glu Glu Ile Gln Gln Asp Ala Tyr Leu Arg
```

```
                        65                  70                  75                  80
                Gln Lys Gln Glu Glu Lys Gln Arg Tyr Met Glu Met Ala Lys Asn Arg
                                85                  90                  95

Asp Gln Ile Ile Ala Leu Leu Lys Lys Gln Arg Asp Glu Arg Ile Lys
                            100                 105                 110

Ile Ser Val Asp Asn Arg Thr Gly
                        115                 120

<210> SEQ ID NO 15
<211> LENGTH: 735
<212> TYPE: DNA
<213> ORGANISM: Gallus gallus
<220> FEATURE:
<221> NAME/KEY: CDS
<222> LOCATION: (290)..(733)

<400> SEQUENCE: 15
gaaagcccag tgggagcaca caggaattca tcttctgagc aaagggaatc tttctcttctt        60 cccaaaatct gtacacatag gccgtgctga tctcagcctt gggcttgcca aactctgcgt       120
ccgcctacac gtgttgaaga aatgcaattc agccctacag gtttctaaat caaaacaaac       180 gttttttgtca tcagtgtgaa cagcagagcc ccagcgcggg ctgacgggaa cgtgccagca       240
gagcaggcag cgccgtgccc aggctgcggg gcaggactgg ggccaccag atg gag ggg        298
                                                     Met Glu Gly
                                                      1 ggc cat cgg ggc gca gcc tca cgt gtc ccc acg agc aca aag cct gat         346
Gly His Arg Gly Ala Ala Ser Arg Val Pro Thr Ser Thr Lys Pro Asp
 5                  10                  15 ggg cac ctc gtc ttt gcc ggc tcg agc cca gct cat gtg gag ttc gcc         394
Gly His Leu Val Phe Ala Gly Ser Ser Pro Ala His Val Glu Phe Ala
20                  25                  30                  35 cgc atc ttc tgg agc acc gcc gtg ctg ccg ccg ctg ctc gag tcc tcc         442
Arg Ile Phe Trp Ser Thr Ala Val Leu Pro Pro Leu Leu Glu Ser Ser
                40                  45                  50 ctg ggt ccc acc aag ctg tgg cgt gag gga cct tcc cct ggg cag acc         490
Leu Gly Pro Thr Lys Leu Trp Arg Glu Gly Pro Ser Pro Gly Gln Thr
            55                  60                  65 cca tct cct ggg cag acc ccg gcc cac aga cgg acc cca tca gct gct         538
Pro Ser Pro Gly Gln Thr Pro Ala His Arg Arg Thr Pro Ser Ala Ala
        70                  75                  80 ctc agc gtg cag aaa gct gaa gca aaa gca aaa tat ggc cag cag gcc         586
Leu Ser Val Gln Lys Ala Glu Ala Lys Ala Lys Tyr Gly Gln Gln Ala
    85                  90                  95 aag aag aga gaa gaa ata ttg gct ttg ctg agg aag cag aga gca gaa         634
Lys Lys Arg Glu Glu Ile Leu Ala Leu Leu Arg Lys Gln Arg Ala Glu
100                 105                 110                 115 agg atc gcg aaa gag ctg att tct cgt cca cat aaa cca aag atg aaa         682
Arg Ile Ala Lys Glu Leu Ile Ser Arg Pro His Lys Pro Lys Met Lys
                120                 125                 130 agc gat caa gta agc agg cag aag gcg ttt gaa gct gag cgt gag gac         730
Ser Asp Gln Val Ser Arg Gln Lys Ala Phe Glu Ala Glu Arg Glu Asp
            135                 140                 145 caa ga                                                                  735
Gln

<210> SEQ ID NO 16
<211> LENGTH: 148
<212> TYPE: PRT
<213> ORGANISM: Gallus gallus
```

<400> SEQUENCE: 16

```
Met Glu Gly Gly His Arg Gly Ala Ala Ser Arg Val Pro Thr Ser Thr
1               5                   10                  15

Lys Pro Asp Gly His Leu Val Phe Ala Gly Ser Ser Pro Ala His Val
            20                  25                  30

Glu Phe Ala Arg Ile Phe Trp Ser Thr Ala Val Leu Pro Pro Leu Leu
        35                  40                  45

Glu Ser Ser Leu Gly Pro Thr Lys Leu Trp Arg Glu Gly Pro Ser Pro
    50                  55                  60

Gly Gln Thr Pro Ser Pro Gly Gln Thr Pro Ala His Arg Arg Thr Pro
65                  70                  75                  80

Ser Ala Ala Leu Ser Val Gln Lys Ala Glu Ala Lys Ala Lys Tyr Gly
                85                  90                  95

Gln Gln Ala Lys Lys Arg Glu Glu Ile Leu Ala Leu Leu Arg Lys Gln
            100                 105                 110

Arg Ala Glu Arg Ile Ala Lys Glu Leu Ile Ser Arg Pro His Lys Pro
        115                 120                 125

Lys Met Lys Ser Asp Gln Val Ser Arg Gln Lys Ala Phe Glu Ala Glu
    130                 135                 140

Arg Glu Asp Gln
145
```

```
<210> SEQ ID NO 17
<211> LENGTH: 504
<212> TYPE: DNA
<213> ORGANISM: Pan troglodytes
<220> FEATURE:
<221> NAME/KEY: CDS
<222> LOCATION: (1)..(501)
```

<400> SEQUENCE: 17

```
atg gaa acg gga ccc agc gaa gaa ctt agc ggc cga aaa gag tcc cag    48
Met Glu Thr Gly Pro Ser Glu Glu Leu Ser Gly Arg Lys Glu Ser Gln
1               5                   10                  15 gaa atg tgc ccc ccg gga tta ctg gta ttt gct ggc tcc tcg gaa caa    96
Glu Met Cys Pro Pro Gly Leu Leu Val Phe Ala Gly Ser Ser Glu Gln
            20                  25                  30 gat gcc aac ttg gct aag cag ttc tgg atc tcg gcg tcg atg tat ccc   144
Asp Ala Asn Leu Ala Lys Gln Phe Trp Ile Ser Ala Ser Met Tyr Pro
        35                  40                  45 cct agc gaa tct cag ctg gtg ctg cgc aga gac agc agt cag cgt ctg   192
Pro Ser Glu Ser Gln Leu Val Leu Arg Arg Asp Ser Ser Gln Arg Leu
    50                  55                  60 ccg gtg gcg cgg ccc agg agg agc aga ggg tct gaa aac agt cac tcc   240
Pro Val Ala Arg Pro Arg Arg Ser Arg Gly Ser Glu Asn Ser His Ser
65                  70                  75                  80 tcg cag tct ttt cac ctt gcg agt aac aaa aat aga gac atc ttt gcc   288
Ser Gln Ser Phe His Leu Ala Ser Asn Lys Asn Arg Asp Ile Phe Ala
                85                  90                  95 gaa gcc cta aag ata cag gaa tct gcg gag aaa gta aag tat ctc caa   336
Glu Ala Leu Lys Ile Gln Glu Ser Ala Glu Lys Val Lys Tyr Leu Gln
            100                 105                 110 aag gta ggc caa tat ttc aga aga cac cca ctt ttt tct ttc ttt aaa   384
Lys Val Gly Gln Tyr Phe Arg Arg His Pro Leu Phe Ser Phe Phe Lys
        115                 120                 125 cag gct aaa aca aga gaa gag att ctc cag ctc tta aga aaa caa aga   432
Gln Ala Lys Thr Arg Glu Glu Ile Leu Gln Leu Leu Arg Lys Gln Arg
    130                 135                 140
```

```
gaa gaa agg atc tcg aaa gaa ctg att tcc ctt ccg tat aaa cca aaa     480
Glu Glu Arg Ile Ser Lys Glu Leu Ile Ser Leu Pro Tyr Lys Pro Lys
145                 150                 155                 160 gcc aaa gaa cac aaa gca aag taa                                    504
Ala Lys Glu His Lys Ala Lys
                165
```

<210> SEQ ID NO 18
<211> LENGTH: 167
<212> TYPE: PRT
<213> ORGANISM: Pan troglodytes

<400> SEQUENCE: 18

```
Met Glu Thr Gly Pro Ser Glu Glu Leu Ser Gly Arg Lys Glu Ser Gln
1               5                   10                  15

Glu Met Cys Pro Pro Gly Leu Leu Val Phe Ala Gly Ser Ser Glu Gln
            20                  25                  30

Asp Ala Asn Leu Ala Lys Gln Phe Trp Ile Ser Ala Ser Met Tyr Pro
        35                  40                  45

Pro Ser Glu Ser Gln Leu Val Leu Arg Arg Asp Ser Ser Gln Arg Leu
    50                  55                  60

Pro Val Ala Arg Pro Arg Arg Ser Arg Gly Ser Glu Asn Ser His Ser
65                  70                  75                  80

Ser Gln Ser Phe His Leu Ala Ser Asn Lys Asn Arg Asp Ile Phe Ala
                85                  90                  95

Glu Ala Leu Lys Ile Gln Glu Ser Ala Glu Lys Val Lys Tyr Leu Gln
            100                 105                 110

Lys Val Gly Gln Tyr Phe Arg Arg His Pro Leu Phe Ser Phe Phe Lys
        115                 120                 125

Gln Ala Lys Thr Arg Glu Glu Ile Leu Gln Leu Leu Arg Lys Gln Arg
    130                 135                 140

Glu Glu Arg Ile Ser Lys Glu Leu Ile Ser Leu Pro Tyr Lys Pro Lys
145                 150                 155                 160

Ala Lys Glu His Lys Ala Lys
                165
```

<210> SEQ ID NO 19
<211> LENGTH: 19
<212> TYPE: DNA
<213> ORGANISM: Mus musculus

<400> SEQUENCE: 19
gatcgggtgc cttgagctt                                                19

<210> SEQ ID NO 20
<211> LENGTH: 22
<212> TYPE: DNA
<213> ORGANISM: Mus musculus

<400> SEQUENCE: 20
acctctgccc ctctcttctt ct                                            22

<210> SEQ ID NO 21
<211> LENGTH: 23
<212> TYPE: DNA
<213> ORGANISM: Mus musculus

<400> SEQUENCE: 21
caaccccacc ctaccctgcc ctg                                           23

```
<210> SEQ ID NO 22
<211> LENGTH: 28
<212> TYPE: DNA
<213> ORGANISM: Mus musculus

<400> SEQUENCE: 22
caaatcaaag gaagttttat cagagtca                                          28

<210> SEQ ID NO 23
<211> LENGTH: 27
<212> TYPE: DNA
<213> ORGANISM: Mus musculus

<400> SEQUENCE: 23
gtcgatacca tatgtcaatc aaatcat                                           27

<210> SEQ ID NO 24
<211> LENGTH: 29
<212> TYPE: DNA
<213> ORGANISM: Mus musculus

<400> SEQUENCE: 24
ccaaggcttt gacttcttct tggtcccctt                                        29

<210> SEQ ID NO 25
<211> LENGTH: 21
<212> TYPE: RNA
<213> ORGANISM: Artificial
<220> FEATURE:
<223> OTHER INFORMATION: siRNA

<400> SEQUENCE: 25
gaaaggaucu cgaaagaacu u                                                 21

<210> SEQ ID NO 26
<211> LENGTH: 21
<212> TYPE: RNA
<213> ORGANISM: Artificial
<220> FEATURE:
<223> OTHER INFORMATION: siRNA

<400> SEQUENCE: 26
gaagagagag caaaguaucu u                                                 21

<210> SEQ ID NO 27
<211> LENGTH: 21
<212> TYPE: RNA
<213> ORGANISM: Artificial
<220> FEATURE:
<223> OTHER INFORMATION: siRNA

<400> SEQUENCE: 27
gcggaacucu aaagucguuu u                                                 21

<210> SEQ ID NO 28
<211> LENGTH: 21
<212> TYPE: RNA
<213> ORGANISM: Artificial
<220> FEATURE:
<223> OTHER INFORMATION: siRNA

<400> SEQUENCE: 28
caaaggaagu uuuaucagau u                                                 21
```

-continued

```
<210> SEQ ID NO 29
<211> LENGTH: 25
<212> TYPE: RNA
<213> ORGANISM: Artificial
<220> FEATURE:
<223> OTHER INFORMATION: siRNA

<400> SEQUENCE: 29
ggaugccaau uuggcuaagc aguuu                                              25

<210> SEQ ID NO 30
<211> LENGTH: 25
<212> TYPE: RNA
<213> ORGANISM: Artificial
<220> FEATURE:
<223> OTHER INFORMATION: siRNA

<400> SEQUENCE: 30
ccuuugauca ggacaaggau gcaau                                              25

<210> SEQ ID NO 31
<211> LENGTH: 21
<212> TYPE: DNA
<213> ORGANISM: Artificial
<220> FEATURE:
<223> OTHER INFORMATION: siRNA

<400> SEQUENCE: 31
cccuauucuc cuucuucgct t                                                  21
```

METHOD FOR DETERMINING GENOTOXICITY

This application claims priority from U.S. Ser. No. 60/630,672, filed Nov. 24, 2004.

FIELD OF THE INVENTION

The present invention relates to the fields of molecular biology and toxicology. More specifically, the present invention relates to methods for determining genotoxicity in compounds, and test cells, transgenic animals, kits and reagents therefore.

BACKGROUND OF THE INVENTION

The mammalian cellular response to genotoxic damage is often analyzed using a battery of tests, which often include in vitro chromosomal aberration or micronuclei formation tests. Both of these tests visualize DNA damage in cells after exposure to potential genotoxicants by analyzing harvested chromosomes for aberrations (S. M. Galloway, *Environ Mol Mutagen* (2000) 35:191-201) or by examining micronuclei formed in cells whose DNA has been damaged (W. von der Hude et al., *Mutation Res* (2000) 468:137-63). However, there are significant problems with interpreting the results of the currently used in vitro genotoxic tests. False positive results in these tests are not uncommon, and the subsequent analysis, which involves in vivo animal testing, can be costly and time consuming. Assays which can better predict the genotoxic potential of a compound are needed (see, e.g., R. K. Newton et al., *Environ Health Persp* (2004) 112:420-22). In response to genotoxic stress, cycling cells that are undergoing cellular differentiation are arrested at discrete stages in the cell cycle (see, e.g., T. Weinert et al., *Nature Gen* (1999) 21:151-52; T. Weinert, *Cell* (1998) 94:555-58). This differentiation arrest is thought to result from activation of key regulatory kinases and other components in response to DNA damage at critical checkpoints in the cell cycle (T. Weinert (1998) supra; B. S. Zhou-Bin et al., *Nature Rev Cancer* (2004) 4:216-25).

P. L. Puri et al., *Nature Gen* (2002) 32:585-93 investigated the ability of four known genotoxic agents (methyl-methane sulfonate, cisplatin, etoposide, and ionizing radiation) to inhibit the differentiation of C2C12 myoblast cells into myotubes. Effects of the agents were also examined by assaying the expression of muscle-specific proteins (myogenin, myosin heavy chain, MyoD), and using a luciferase reporter gene coupled to the muscle creatinine kinase promoter.

The murine gene DDA3 was sequenced for study due to its regulation by p53 (P.-K. Lo et al., *Oncogene* (1999) 18:7765-74). P-K Lo et al. also found that DDA3 was upregulated in NIH3T3 cells exposed to DNA damaging agents such as adriamycin and mitomycin C. P-K Lo et al. found that DDA3 was strongly expressed in brain, spleen, and lung (with moderate expression in kidney): no expression or minimal expression was found in heart, liver, skeletal muscle, or testis. The 5' genomic sequence (including the upstream regulatory region) was sequenced and described by S.-C. Hsieh et al., *Oncogene* (2002) 21:3050-57, who identified the p53-binding element and determined that expression was also induced by p73. P.-K. Lo & F.-F. Wang, *Biochim Biophys Acta* (2002) 1579:214-18 reported the identification and sequencing of the human DDA3 homolog, also finding that it was expressed in nearly every tissue except adult skeletal muscle. P.-K. Lo & F.-F. Wang, *Arch Biochem Biophys* (2004) 425:221-32 reported that murine DDA3 is transcribed or edited into a number of different forms.

Tugendreich et al., WO2004/037200, disclosed the measurement of genomic responses of rat liver cells to hydroxyurea, cytarabine, doxorubicin, ifosfamide, thioguanine, azathioprine, etoposide, and albendazole, each administered in vivo. The genomic responses were then used to derive a "drug signature" that correlates the transcriptional regulation of two genes (aminolevulinate synthase 2 delta, Genbank NM 013197; and peripherin 1, Genbank NM 012633) with the propensity of each compound to cause depletion of reticulocytes.

SUMMARY OF THE INVENTION

We have now determined that several genes are activated in eukaryotic cells that are capable of further differentiation when such cells are exposed to DNA-damaging (genotoxic) agents followed by induction of differentiation.

One aspect of the invention comprises a method for determining the genotoxicity of a test compound, by contacting a cell capable of differentiation with the test compound, inducing differentiation, and determining the expression level of one or more indicator genes.

Another aspect of the invention comprises a kit for determining the genotoxicity of a test compound, comprising a suitable cell capable of differentiation, and reagents for quantifying the expression levels of selected indicator genes.

Another aspect of the invention comprises a polynucleotide capable of specifically hybridizing to a polynucleotide having the sequence of SEQ ID NO: 5, 7, 9, 11, 13, 15, or 17, or the complement thereof. Another aspect of the invention comprises a set of polynucleotides capable of specifically hybridizing to a plurality of selected indicator genes.

Another aspect of the invention is a microarray comprising a set of polynucleotides capable of specifically hybridizing to a plurality of selected indicator genes.

Another aspect of the invention comprises a polypeptide having the sequence of SEQ ID NO:6, 8, 10, 12, 14, 16, or 18.

Another aspect of the invention comprises an antibody capable of specifically binding to a polypeptide having the sequence of SEQ ID NO: 6, 8, 10, 12, 14, 16, or 18.

Another aspect of the invention comprises a transgenic non-human mammal in which a reporter gene is operably linked to an indicator gene.

DETAILED DESCRIPTION OF THE INVENTION

All publications cited in this disclosure are incorporated herein by reference in their entirety.

Definitions

Unless otherwise stated, the following terms used in this Application, including the specification and claims, have the definitions given below. It must be noted that, as used in the specification and the appended claims, the singular forms "a", "an," and "the" include plural referents unless the context clearly dictates otherwise.

The term "test cell" refers to a cell such as a blast cell that is capable of further differentiation, for example to a terminally differentiated state such as a myotubule, adipocyte, erythrocyte, or the like. Test cells are preferably derived from vertebrates such as, for example, zebra fish (*Danio rerio*), chickens (*Gallus gallus*), mouse (*Mus musculus*), rat (*Rattus norvegicus*), chimpanzees (*Pan troglodytes*), human (*Homo sapiens*), and the like. "Test cells" include both primary cell samples and established cell lines, whether recombinant or wild type. Exemplary test cells include, without limitation, mouse C2C12 cells, rat L6E9 cells, pre-adipocytes, 3T3-L1 cells, osteoblasts, and the like. Test cells can be modified to express a detectable label in addition to, or in lieu of, the indicator gene. For example, the test cell can be stably transfected with a construct comprising the regulatory sequences derived from an indicator gene, operably linked to a detectable label gene such as luciferase, green fluorescent protein (GFP), β-galactosidase (βGal), horseradish peroxidase (HRP), or the like.

The term "test sample" refers to a substance, mixture, or test condition with which the test cell can be contacted or treated, for purposes of evaluating the genotoxicity thereof. The method of the invention is useful for evaluating the genotoxic effect of substances other than pure compounds and solutions, and thus can be used to test, for example, radiation; environmental samples (for example of polluted air, water, or soil); viruses or other micro-organisms; proteins, polynucleotides, polymers and other macromolecules; and the like. The test cells can be "contacted" with conditions such as radiation by exposing the cell to said conditions in a way that permits the cell to react.

The term "indicator gene" refers to a gene in which modulation of the expression level correlates with genotoxicity (DNA damage). Indicator genes within the scope of this invention include DDA3 (SEQ ID NO:1, SEQ ID NO:3), 4833427G06Rik (SEQ ID NO:5, 7, 9, 11, 13, 15, OR 17), and the genes listed in Table 2 below.

The terms "promoter" and "regulatory region" are used interchangeably herein to refer to polynucleotide sequences that bind transcription factors and transcriptases, regulating the expression of an indicator gene. Promoters are found adjacent to (cis) and (usually) upstream from the coding regions or structural gene.

The term "reporter gene" as used herein refers to a gene that encodes a detectable product. A "reporter gene" is a gene that, upon expression, confers a phenotype on a cell expressing the reporter gene such that the cell can be identified under appropriate conditions. In the present case, the reporter gene is operably linked to a promoter or regulatory sequence, such that expression of the reporter gene indicates activation of the promoter or regulatory sequence. A "heterologous reporter gene" is a reporter gene that is operably linked to a promoter or regulatory region different from the promoter or regulatory region to which it is linked in nature. For example, the reporter gene can produce a polypeptide product that can be easily detected or measured in a routine assay. Suitable reporter genes known in the art which confer this characteristic include those that encode chloramphenicol acetyl transferase (CAT activity), β-galactosidase, luciferase, alkaline phosphatase, human growth hormone, fluorescent proteins, such as green fluorescent protein (GFP), and others. Indeed, any gene that encodes a protein or enzyme that can readily be measured, for example, by an immunoassay such as an enzyme-linked immunosorbent assay (ELISA) or by the enzymatic conversion of a substrate into a detectable product, and that is substantially not expressed in the host cells (specific expression with no background) can be used as a reporter gene to test for promoter activity. Other reporter genes for use herein include genes that allow selection of cells based on their ability to thrive in the presence or absence of a chemical or other agent that inhibits an essential cell function. Suitable markers, therefore, include genes coding for proteins which confer drug resistance or sensitivity thereto, or change the antigenic characteristics of those cells expressing the reporter gene when the cells are grown in an appropriate selective medium. For example, reporter genes include: cytotoxic and drug resistance markers, whereby cells are selected by their ability to grow on media containing one or more of the cytotoxins or drugs; auxotrophic markers by which cells are selected by their ability to grow on defined media with or without particular nutrients or supplements; and metabolic markers by which cells are selected for, e.g., their ability to grow on defined media containing the appropriate sugar as the sole carbon source. These and other reporter genes are well known in the art.

A "change in the level of reporter gene product" is shown by comparing expression levels of the reporter gene product in a cell exposed to a candidate compound relative to the levels of reporter gene product expressed in a cell that is not exposed to the test compound and/or to a cell that is exposed to a control compound. The change in level can be determined quantitatively for example, by measurement using a spectrophotometer, spectrofluorometer, luminometer, and the like, and will generally represent a statistically significant increase or decrease in the level from background. However, such a change can also be noted without quantitative measurement simply by, e.g., visualization, such as when the reporter gene is one that confers the ability on cells to form colored colonies on chromogenic substrates.

The term "operably linked" indicates a functional relationship between a promoter or regulatory region and a regulated structural gene, such that activation of the promoter or regulatory region leads to increased transcription of the structural gene.

The term "Dda3" or "DDA3" refers to the polynucleotide having the sequence of SEQ ID NO:1 (murine) or SEQ ID NO:3 (human). "Homologs" of DDA3 are polynucleotides (for example, RNA, cDNA or genomic DNA) that are derived from other species and have a similar sequence to murine and/or human Dda3 (sense strand or complement), having a sequence identity of at least 60%. Homologs of the murine and/or human DDA3 protein are polypeptides derived from other species having at least 60% sequence identity with murine or human DDA3 protein (SEQ ID NO:2 or SEQ ID NO:4, respectively).

The term "4833427G06Rik" refers to the polynucleotide having the sequence of SEQ ID NO:5 (murine), SEQ ID NO:7 (human), SEQ ID NO:9 (rat), SEQ ID NO:11 (zebra fish), SEQ ID NO:13 (the second zebra fish homolog), SEQ ID NO:15 (chicken), or SEQ ID NO:17 (chimpanzee). "Homologs" of 4833427G06Rik are polynucleotides (for example, RNA, cDNA or genomic DNA) that are derived from other species and have a similar sequence to murine and/or human 4833427G06Rik (sense strand or complement), having a sequence identity of at least 60%. Homologs of the murine and/or human 4833427G06Rik protein are polypeptides derived from other species having at least 60% sequence identity with murine or human 4833427G06Rik protein (SEQ ID NO:6 or SEQ ID NO:8, respectively). "4833427G06Rik" can also be referred to as "Dog1" ("discriminator of genotoxicity 1").

The term "specific hybridization" as used herein refers to the binding of complementary strands of nucleic acid to each other through hydrogen bonds. Stringency levels used to hybridize a given probe with target DNA can be readily varied by those of skill in the art. The phrase "stringent hybridization" is used herein to refer to conditions under which double-stranded polynucleotide molecules are stable only when highly complementary, having few base mismatches, as reflected in the melting temperature ($T_m$) of the double-stranded ("ds") polynucleotides. In general, the stability of a ds polynucleotide is a function of sodium ion concentration and temperature. Typically, a hybridization reaction is performed under conditions of lower stringency, followed by washes of increasing stringency. Reference to hybridization stringency relates to such washing conditions.

As used herein, the phrase "moderately stringent hybridization" refers to conditions that permit target-DNA to bind a complementary nucleic acid that has about 60% identity, preferably about 75% identity, more preferably about 85% identity to the target DNA; with greater than about 90% identity to target-DNA being preferred. Moderately stringent conditions are conditions equivalent to hybridization in 50% formamide, 5×Denhart's solution, 5×SSPE, 0.2% SDS at 42° C., followed by washing in 0.2×SSPE, 0.2% SDS, at 65° C. The phrase "high stringency hybridization" refers to conditions that permit hybridization of only those nucleic acid sequences that form stable hybrids in 0.018 M NaCl at 65° C. (i.e., if a hybrid is not substantially stable in 0.018 M NaCl at 65° C., it will not be stable under high stringency conditions, as contemplated herein). High stringency conditions can be provided, for example, by hybridization in 50% formamide, 5× Denhart's solution, 5×SSPE, 0.2% SDS at 42° C., followed by washing in 0.1×SSPE, and 0.1% SDS at 65° C. The phrase "low stringency hybridization" refers to conditions equivalent to hybridization in 10% formamide, 5× Denhart's solution, 6×SSPE, 0.2% SDS at 42° C., followed by washing in 1×SSPE, 0.2% SDS, at 50° C. Denhart's solution and SSPE (see, e.g., Sambrook et al., Molecular Cloning, A Laboratory Manual, Cold Spring Harbor Laboratory Press, 1989) are well known to those of skill in the art as are other suitable hybridization buffers.

The term "specifically binding" between two entities means an affinity of at least $10^7$ $M^{-1}$.

The term "substantial identity" means that two polynucleotide or polypeptide sequences, when optimally aligned, such as by the programs GAP or BESTFIT using default gap weights, share at least 65% sequence identity, preferably at least 80% or 90% sequence identity, more preferably at least 95% sequence identity or more (e.g., 99% sequence identity or higher). In the case of polypeptides, residue positions which are not identical preferably differ by conservative amino acid substitutions. For sequence comparison, typically one sequence acts as a reference sequence to which test sequences are compared. When using a sequence comparison algorithm, test and reference sequences are entered into a computer, subsequence coordinates are designated (if necessary), and sequence algorithm program parameters are designated. The sequence comparison algorithm then calculates the percent sequence identity for the test sequence(s) relative to the reference sequence, based on the designated program parameters. Optimal alignment of sequences for comparison can be conducted, e.g., by the local homology algorithm of Smith & Waterman, *Adv. Appl. Math.* (1981) 2:482, by the homology alignment algorithm of Needleman & Wunsch, *J. Mol. Biol.* (1970) 48:443, by the search for similarity method of Pearson & Lipman, *Proc Natl Acad Sci USA* (1988) 85:2444, by computerized implementations of these algorithms (GAP, BESTFIT, FASTA, and TFASTA in the Wisconsin Genetics Software Package, Genetics Computer Group, 575 Science Dr., Madison, Wis.), or by visual inspection. One example of an algorithm that is suitable for determining percent sequence identity and sequence similarity is the BLAST algorithm, described by Altschul et al., *J. Mol. Biol.* (1990) 215:403-10. Software for performing BLAST analyses is publicly available through the National Center for Biotechnology Information (www.ncbi.nlm.nih.gov/). Typically, default program parameters are used to perform the sequence comparison, although customized parameters can also be used. For amino acid sequences, the BLASTP program uses as defaults a wordlength (W) of 3, an expectation (E) of 10, and the BLOSUM62 scoring matrix (see Henikoff & Henikoff, *Proc. Natl. Acad. Sci. USA* (1989) 89:10915).

For purposes of classifying amino acids substitutions as conservative or nonconservative, amino acids are grouped as follows: Hydrophobic sidechains: norleucine, met, ala, val, leu, ile; Neutral hydrophilic side chains: cys, ser, thr; Acidic side chains: asp, glu; Basic side chains: asn, gln, his, lys, arg; Residues influencing chain orientation: gly, pro; and Aromatic side chains: trp, tyr, phe. Conservative substitutions involve substitutions between amino acids in the same class. Non-conservative substitutions constitute exchanging a member of one of these classes for a member of another.

The term "antibody" or "immunoglobulin" is used to include intact antibodies and binding fragments thereof. Typically, fragments compete with the intact antibody from which they were derived for specific binding to an antigen fragment including separate heavy chains, light chains Fab, Fab' F(ab')$_2$, Fabc, and Fv. Fragments are produced by recombinant DNA techniques, or by enzymatic or chemical separation of intact immunoglobulins. The term "antibody" also includes one or more immunoglobulin chains that are chemically conjugated to or expressed as fusion proteins with other proteins. The term "antibody" also includes bispecific antibodies. A bispecific or bifunctional antibody is an artificial hybrid antibody having two different heavy/light chain pairs and two different binding sites. Bispecific antibodies can be produced by a variety of methods including fusion of hybridomas or linking of Fab' fragments. See, e.g., Songsivilai & Lachmann, *Clin. Exp. Immunol.* (1990) 79:315-21; Kostelny et al., *J. Immunol.* (1992) 148:1547-53. An "antigen" is an entity to which an antibody specifically binds.

The term "epitope" or "antigenic determinant" refers to a site on an antigen to which B and/or T cells respond. B-cell epitopes can be formed both from contiguous amino acids or noncontiguous amino acids juxtaposed by tertiary folding of a protein Epitopes formed from contiguous amino acids are typically retained on exposure to denaturing solvents whereas epitopes formed by tertiary folding are typically lost on treatment with denaturing solvents. An epitope typically includes at least 3, and more usually, at least 5 or 8-10 amino acids in a unique spatial conformation. Methods of determining spatial conformation of epitopes include, for example, x-ray crystallography and 2-dimensional nuclear magnetic resonance. See, e.g., Epitope Mapping Protocols in Methods in Molecular Biology, Vol. 66, Glenn E. Morris, Ed. (1996). Antibodies that recognize the same epitope can be identified in a simple immunoassay showing the ability of one antibody to block the binding of another antibody to a target antigen. T-cells recognize continuous epitopes of about nine amino acids for CD8 cells or about 13-15 amino acids for CD4 cells. T cells that recognize the epitope can be identified by in vitro assays that measure antigen-dependent proliferation, as determined by $^3$H-thymidine incorporation by primed T cells in response to an epitope (Burke et al., *J. Inf. Dis.* (1994) 170:1110-19), by antigen-dependent killing (cytotoxic T lymphocyte assay, Tigges et al., *J. Immunol.* (1996) 156: 3901-10) or by cytokine secretion.

An "immunogenic agent" or "immunogen" is capable of inducing an immunological response against itself on administration to a mammal, optionally in conjunction with an adjuvant. The term "adjuvant" refers to a compound that when administered in conjunction with an antigen augments the immune response to the antigen, but when administered alone does not generate an immune response to the antigen. Adjuvants can augment an immune response by several mechanisms including lymphocyte recruitment, stimulation of B and/or T cells, and stimulation of macrophages.

Competition between antibodies is determined by an assay in which the immunoglobulin under test inhibits specific binding of a reference antibody to a common antigen. Numerous types of competitive binding assays are known, for example: solid phase direct or indirect radioimmunoassay (RIA), solid phase direct or indirect enzyme immunoassay (EIA), sandwich competition assay (see Stahli et al., *Meth Enzymol* (1983) 9:242-53); solid phase direct biotin-avidin EIA (see Kirkland et al., *J. Immunol.* (1986) 137:3614-19); solid phase direct labeled assay, solid phase direct labeled sandwich assay (see Harlow and Lane, "Antibodies, A Laboratory Manual," Cold Spring Harbor Press (1988)); solid phase direct label RIA using $^{125}$I label (see Morel et al., *Mol. Immunol.* (1988) 25(1):7-15); solid phase direct biotin-avidin EIA (Cheung et al., *Virology* (1990) 176:546-52); and direct labeled RIA (Moldenhauer et al., *Scand. J. Immunol.* (1990) 32:77-82). Typically, such an assay involves the use of purified antigen bound to a solid surface or cells bearing either of these, an unlabelled test immunoglobulin and a labeled reference immunoglobulin. Competitive inhibition is measured by determining the amount of label bound to the solid surface or cells in the presence of the test immunoglobulin. Usually the test immunoglobulin is present in excess. Antibodies identified by competition assay (competing antibodies) include antibodies binding to the same epitope as the reference antibody and antibodies binding to an adjacent epitope sufficiently proximal to the epitope bound by the reference antibody for steric hindrance to occur. Usually, when a competing antibody is present in excess, it will inhibit specific binding of a reference antibody to a common antigen by at least 50 or 75%.

"Treating" or "treatment" of a disease includes: (1) preventing the disease, i.e., causing the clinical symptoms of the disease not to develop in a mammal that can be exposed to or predisposed to the disease but does not yet experience or display symptoms of the disease; (2) inhibiting the disease, i.e., arresting or reducing the development of the disease or its clinical symptoms; or (3) relieving the disease, i.e., causing regression of the disease or its clinical symptoms.

"A therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

"Modulator" means a molecule that interacts with a target. The interactions include, but are not limited to, agonist, antagonist, and the like, as defined herein.

"Optional" or "optionally" means that the subsequently described event or circumstance may but need not occur, and that the description includes instances where the event or circumstance occurs and instances in which it does not.

"Disease state" means any disease, condition, symptom, or indication.

"Subject" means mammals and non-mammals. Mammals means any member of the mammalia class including, but not limited to, humans; non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like. The term "subject" does not denote a particular age or sex.

The term "transgenic animal" or "knockout animal" refers to an engineered animal having dysfunctional expression of a target gene or genes, or having expression of a heterologous gene.

General Method

The invention provides a method for detecting genotoxicity in a compound. In essence, test cells are provided which are capable of further differentiation. The test cells are contacted with a test compound or test sample, and incubated for a period of time sufficient for the test compound or test sample to interact with the test cell. The test cell is then induced to differentiate, and the change in expression level of one or more indicator genes is determined.

A suitable test cell is first selected. In general, the test cell used will be capable of further differentiation to an intermediate or terminally-differentiated form, and can comprise a cell line, tissue sample, isolate or explant, and the like. The test cell can be present as a part of the population of cells in a sample or isolate. Alternatively, the cellular response can be studied in situ, administering the test compounds to an animal, particularly a transgenic animal. Preferably, a permanent cell line such as C2C12 is employed.

The suitable cell can be modified by incorporating a reporter construct, for example by replacing the structural DDA3 gene or the coding region of 4833427G06Rik with a reporter gene, e.g., by homologous recombination, or by transforming the cell with a construct having an indicator gene regulatory region operably linked to a reporter gene. One can utilize any of the genes listed in Table 2, or combinations thereof. Additionally, one can use a panel of two or more different test cells, where each test cell comprises a reporter construct responsive to the regulatory regions of one or more indicator genes. Where the reporter construct provides an observable label, such as green fluorescent protein (GFP), β-galactosidase (βGal), or the like, each test cell preferably comprises no more than two reporter constructs, more preferably no more than one reporter construct. Where the reporter construct provides a transcription label (e.g., a distinct polynucleotide sequence), the cell can contain multiple reporter constructs. In either case, a panel of test cells can be constructed having different types of test cell (for example, myoblasts and osteoblasts), and/or test cells derived from different species (e.g., mouse and human cells).

The particular indicator genes to be assayed are preferably selected on the basis of their selectivity, i.e., they should exhibit a strong response to exposure to genotoxic compounds or conditions, and little or no response to compounds or conditions that are not genotoxic. The "strong response" can be either up-regulation or down-regulation, and is generally evaluated by comparison to the degree of variation in signal in the absence of a genotoxic compound or condition (e.g., by comparison to the "background noise" of the gene). Preferably, the indicator genes used comprise DDA3 and 4833427G06Rik.

The compounds to be tested can be derived from any source, and can be provided as pure compounds or solutions, mixtures, formulated drugs, complex environmental samples (for example, a water or soil sample suspected of containing genotoxic agents), and the like. In the case of pure compounds, such as for example drug candidates, one preferably prepares a series of dilutions, generally limited by the lowest concentration at which an effect can be observed (or the lowest concentration likely to be useful) and the maximum concentration that the selected cells will tolerate (or a dose which is high enough to be toxic). In the case of unknown samples, one will preferably prepare a series of dilutions such as, for example 1:10, 1:30, 1:100, 1:300, and so forth, to determine the potency of any included genotoxic agent. In the case of environmental samples, one can instead first establish a baseline "acceptable" level, and screen samples at that dilution to determine whether or not the sample contains less than the "acceptable" level of genotoxic agents. Environmental samples can optionally be sterilized prior to testing, to avoid possible effects from viruses, bacteria, and fungi that can be present in the sample.

The selected cells are contacted with compounds or samples while being maintained in the resting phase (G0) of the mitotic cycle, and incubated for a period of time sufficient to permit any interaction to occur. In general, this incubation time will be at least about 5 minutes, more preferably at least about 20 minutes, still more preferably at least about 1 hour, still more preferably at least about 4 hours. The incubation time will preferably be less than about 48 hours, more preferably less than about 36 hours, most preferably about 12 to about 24 hours.

After incubation with the compounds or samples, the cells are optionally washed to remove any remaining compound, then exposed to conditions that would induce the cells to differentiate (the cells may or may not arrest, and fail to actually differentiate). The method for inducing differentiation will generally depend on the particular cells employed, but typically involves adding suitable growth factors, often in the form of serum. The cells are permitted to differentiate for a period of time sufficient for a detectable change in the indicator gene expression levels to occur. In general, this differentiation time will be at least about 5 minutes, preferably at least about 20 minutes, still more preferably at least about 1 hour, still more preferably at least about 4 hours. The differentiation time will generally be less than about 48 hours, more preferably less than about 36 hours, most preferably about 12 to about 24 hours.

After exposure to differentiating conditions, the expression level of one or more indicator genes is determined. The expression level can be detected by directly measuring the indicator gene mRNA transcribed (for example, using RT-PCR or other quantitative or semi-quantitative PCR or target amplification methods), by measuring the protein product, by measuring a detectable label expressed under the control of the indicator gene promoter, or by using other methods known in the art. See, e.g., N. Kruse et al., *J Immunol Meth* (1997) 210:195-203, incorporated herein by reference. The protein product can be measured by a variety of methods known in the art, including directly measuring the protein by binding to a selective antibody (after either in vivo or in vitro translation of mRNA), measuring the protein by means of its enzymatic activity or the activity of a fusion protein combining the indicator gene product with a detectable label (for example luciferin, green fluorescent protein, horseradish peroxidase, and the like), and the like.

Where polynucleotides are detected directly, the sequences employed will generally be subsets of the sequences (and complements) set forth in the attached Sequence Listing. The selection of sequence will depend on the species of cells employed, and the details of any constructs used and form of amplification employed. Exemplary sequences for RT-PCR include, without limitation, SEQ ID NO:19, SEQ ID NO:20, SEQ ID NO:22, and SEQ ID NO:23.

The change in expression level is typically determined by comparison to a control expression level, which can be either a historically established average value, or preferably the expression level of a test cell not treated with a genotoxic compound (e.g., treated with vehicle alone) but otherwise treated identically with the other test cells. In general, an increase or decrease in expression level by a factor of 1.5 or greater, preferably a factor of 2.0 or greater, in the expression of an indicator gene signifies that the test compound exhibits genotoxicity.

The gene 4833427G06Rik and its protein product were not previously known to have any activity: our invention here demonstrates that they are involved in cell cycle regulation and differentiation.

The present invention also provides recombinant cloning and expression vectors containing DNA, as well as host cell containing the recombinant vectors. Expression vectors comprising DNA can be used to prepare the polypeptides or fragments of the invention encoded by the DNA. A method for producing polypeptides comprises culturing host cells transformed with a recombinant expression vector encoding the polypeptide, under conditions that promote expression of the polypeptide, then recovering the expressed polypeptides from the culture. The skilled artisan will recognize that the procedure for purifying the expressed polypeptides will vary according to such factors as the type of host cells employed, and whether the polypeptide is membrane-bound or a soluble form that is secreted from the host cell. Any suitable expression system can be employed. The vectors include a DNA encoding a polypeptide or fragment of the invention, operably linked to suitable transcriptional or translational regulatory nucleotide sequences, such as those derived from a mammalian, microbial, viral, or insect gene. Examples of regulatory sequences include transcriptional promoters, operators, or enhancers, an mRNA ribosomal binding site, and appropriate sequences which control transcription and translation initiation and termination. Nucleotide sequences are operably linked when the regulatory sequence functionally relates to the DNA sequence. Thus, a promoter nucleotide sequence is operably linked to a DNA sequence if the promoter nucleotide sequence controls the transcription of the DNA sequence. An origin of replication that confers the ability to replicate in the desired host cells, and a selection gene by which transformants are identified, are generally incorporated into the expression vector.

In addition, a sequence encoding an appropriate signal peptide (native or heterologous) can be incorporated into expression vectors. A DNA sequence for a signal peptide (secretory leader) can be fused in frame to the polynucleotide sequence of the invention so that the DNA is initially transcribed, and the mRNA translated, into a fusion protein comprising the signal peptide. A signal peptide that is functional in the intended host cells promotes extracellular secretion of the polypeptide. The signal peptide is cleaved from the polypeptide upon secretion of polypeptide from the cell.

The skilled artisan will also recognize that the position(s) at which the signal peptide is cleaved may differ from that predicted by computer program, and may vary according to such factors as the type of host cells employed in expressing a recombinant polypeptide. A protein preparation can include a mixture of protein molecules having different N-terminal amino acids, resulting from cleavage of the signal peptide at more than one site.

Suitable host cells for expression of polypeptides include prokaryotes, yeast or higher eukaryotic cells. Mammalian or insect cells are generally preferred for use as host cells. Appropriate cloning and expression vectors for use with bacterial, fungal, yeast, and mammalian cellular hosts are described, for example, in Pouwels et al., "Cloning Vectors: A Laboratory Manual" (Elsevier, New York, 1985). Cell-free translation systems could also be employed to produce polypeptides using RNA derived from DNA constructs disclosed herein.

Prokaryotes include gram-negative or gram-positive organisms. Suitable prokaryotic host cells for transformation include, for example, *E. coli, Bacillus subtilis, Salmonella typhimurium*, and various other species within the genera *Pseudomonas, Streptomyces*, and *Staphylococcus*. In a prokaryotic host cell, such as *E. coli*, a polypeptide can include an N-terminal methionine residue to facilitate expression of the recombinant polypeptide in the prokaryotic host cell. The N-terminal Met may be cleaved from the expressed recombinant polypeptide.

Expression vectors for use in prokaryotic host cells generally comprise one or more phenotypic selectable marker genes. A phenotypic selectable marker gene is, for example, a gene encoding a protein that confers antibiotic resistance or that supplies an autotrophic requirement. Examples of useful expression vectors for prokaryotic host cells include those derived from commercially available plasmids such as the cloning vector pBR322 (ATCC 37017). pBR322 contains genes for ampicillin and tetracycline resistance, and thus provides simple means for identifying transformed cells. An appropriate promoter and a DNA sequence are inserted into the pBR322 vector. Other commercially available vectors include, for example, pKK223-3 (Pharmacia Fine Chemicals, Uppsala, Sweden) and pGEM1 (Promega Biotec, Madison, Wis., USA).

Promoter sequences commonly used for recombinant prokaryotic host cell expression vectors include β-lactamase (penicillinase), lactose promoter system (Chang et al., *Nature* (1978) 275:615; and Goeddel et al., *Nature* (1979) 281:544), tryptophan (trp) promoter system (Goeddel et al., *Nuc Acids Res.* (1980) 8:4057; and EP036776) and tac promoter (Maniatis, "Molecular Cloning: A Laboratory Manual", Cold Spring Harbor Laboratory, p. 412, 1982). A particularly useful prokaryotic host cell expression system employs a phage $\lambda P_L$ promoter and a cI857ts thermolabile repressor sequence. Plasmid vectors available from the American Type Culture Collection which incorporate derivatives of the $\lambda P_L$ promoter include plasmid pHUB2 (resident in *E. coli* strain JMB9, ATCC 37092) and pPLc28 (resident in *E. coli* RR1, ATCC 53082).

Alternatively, the polypeptides can be expressed in yeast host cells, preferably from the *Saccharomyces* genus (e.g., *S. cerevisiae*). Other genera of yeast, such as *Pichia* or *Kluyveromyces*, can also be employed. Yeast vectors will often contain an origin of replication sequence from a 2μ yeast plasmid, an autonomously replicating sequence (ARS), a promoter region, sequences for polyadenylation, sequences for transcription termination, and a selectable marker gene. Suitable promoter sequences for yeast vectors include, among others, promoters for metallothionein, 3-phosphoglycerate kinase (Hitzeman et al., *J. Biol. Chem.* (1980) 255:2073) or other glycolytic enzymes (Hess et al., *J. Adv. Enzyme Reg.* (1968) 7:149; and Holland et al., *Biochem.* (1978) 17:4900), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triose-phosphate isomerase, phospho-glucose isomerase, and glucokinase. Other suitable vectors and promoters for use in yeast expression are further described in Hitzeman, EP073,657. Another alternative is the glucose-repressible ADH2 promoter described by Russell et al., *J. Biol. Chem.* (1982) 258:2674 and Beier et al., *Nature* (1982) 300:724. Shuttle vectors replicable in both yeast and *E. coli* can be constructed by inserting DNA sequences from pBR322 for selection and replication in *E. coli* ($Amp^r$ gene and origin of replication) into the above-described yeast vectors.

The yeast α-factor leader sequence can be employed to direct secretion of the polypeptide. The α-factor leader sequence is often inserted between the promoter sequence and the structural gene sequence. See, e.g., Kurjan et al., *Cell* (1982) 30:933, and Bitter et al., *Proc Natl Acad Sci USA* (1984) 81:5330. Other leader sequences suitable for facilitating secretion of recombinant polypeptides from yeast hosts are known to those of skill in the art. A leader sequence can be modified near its 3' end to contain one or more restriction sites. This will facilitate fusion of the leader sequence to the structural gene.

Yeast transformation protocols are known to those of skill in the art. One such protocol is described by Hinnen et al., *Proc Natl Acad Sci USA* (1978) 75:1929, 1978. The Hinnen et al. protocol selects for $Trp^+$ transformants in a selective medium, wherein the selective medium consists of 0.67% yeast nitrogen base, 0.5% casamino acids, 2% glucose, 10 mg/ml adenine and 20 mg/ml uracil.

Yeast host cells transformed by vectors containing an ADH2 promoter sequence can be grown for inducing expression in a "rich" medium. An example of a rich medium is one consisting of 1% yeast extract, 2% peptone, and 1% glucose supplemented with 80 mg/ml adenine and 80 mg/ml uracil. Derepression of the ADH2 promoter occurs when glucose is exhausted from the medium.

Mammalian or insect host cell culture systems also can be employed to express recombinant polypeptides. Bacculovirus systems for production of heterologous proteins in insect cells are reviewed by Luckow and Summers, *Bio/Technology* (1988) 6:47. Established cell lines of mammalian origin also may be employed. Examples of suitable mammalian host cell lines include the COS-7 line of monkey kidney cells (ATCC CRL 1651) (Gluzman et al., *Cell* (1981) 23:175), L cells, C127 cells, 3T3 cells (ATCC CCL 163), Chinese hamster ovary (CHO) cells, HeLa cells, and BHK (ATCC CRL 10) cell lines, and the CV1/EBNA cell line derived from the African green monkey kidney cell line CV1 (ATCC CCL 70) as described by McMahan et al. (*EMBO J.* (1991) 10:2821).

Established methods for introducing DNA into mammalian cells have been described (Kaufman, R. J., "Large Scale Mammalian Cell Culture", 1990, pp. 15-69). Additional protocols using commercially available reagents, such as Lipofectamine lipid reagent (Gibco/BRL) or Lipofectamine-Plus lipid reagent, can be used to transfect cells (Felgner et al., *Proc Natl Acad Sci USA* (1987) 84:7413-17). In addition, electroporation can be used to transfect mammalian cells using conventional procedures, such as those in Sambrook et al. ("Molecular Cloning: A Laboratory Manual", 2d ed. Vol. 1-3, Cold Spring Harbor Laboratory Press, 1989). Selection of stable transformants can be performed using methods known in the art, such as, for example, resistance to cytotoxic drugs. Kaufman et al., *Meth Enzymol* (1990) 185:487-511, describes several selection schemes, such as dihydrofolate reductase (DHFR) resistance. A suitable host strain for DHFR selection can be CHO strain DX-B11, which is deficient in DHFR (Urlaub and Chasin, *Proc Natl Acad Sci USA* (1980) 77:4216-20). A plasmid expressing the DHFR cDNA can be introduced into strain DX-B11, and only cells that contain the plasmid can grow in the appropriate selective media. Other examples of selectable markers that can be incorporated into an expression vector include cDNAs conferring resistance to antibiotics, such as G418 and hygromycin B. Cells harboring the vector can be selected on the basis of resistance to these compounds.

Transcriptional and translational control sequences for mammalian host cell expression vectors can be excised from viral genomes. Commonly used promoter sequences and enhancer sequences are derived from polyoma virus, adenovirus 2, simian virus 40 (SV40), and human cytomegalovirus. DNA sequences derived from the SV40 viral genome, for example, SV40 origin, early and late promoter, enhancer, splice, and polyadenylation sites can be used to provide other genetic elements for expression of a structural gene sequence in a mammalian host cell. Viral early and late promoters are particularly useful because both are easily obtained from a viral genome as a fragment, which can also contain a viral origin of replication (Fiers et al., *Nature* (1978) 273:113; Kaufman, *Meth. Enzymol* (1990). Smaller or larger SV40 fragments can also be used, provided the approximately 250 bp sequence extending from the Hind III site toward the Bgl I site located in the SV40 viral origin of replication site is included.

Additional control sequences shown to improve expression of heterologous genes from mammalian expression vectors include such elements as the expression augmenting sequence element (EASE) derived from CHO cells (Morris et al., WO 97/25420) and the tripartite leader (TPL) and VA gene RNAs from Adenovirus 2 (Gingeras et al., *J. Biol. Chem.* (1982) 257:13475-91). The internal ribosome entry site (IRES) sequences of viral origin allows dicistronic mRNAs to be translated efficiently (Oh and Sarnow, *Cur Op Gen Dev* (1993) 3:295-300; Ramesh et al., *Polynuc Res* (1996) 24:2697-700). Expression of a heterologous cDNA as part of a dicistronic mRNA followed by the gene for a selectable marker (e.g. DHFR) has been shown to improve transfectability of the host and expression of the heterologous cDNA (Kaufman, *Meth Enzymol,* 1990). Exemplary expression vectors that employ dicistronic mRNAs are pTR-DC/GFP described by Mosser et al., *Biotechniques* (1997) 22:150-61, and p2A5I described by Morris et al., "Animal Cell Technology", 1997, pp. 529-34.

A useful high expression vector, pCAVNOT, has been described by Mosley et al., *Cell* (1989) 59:335-48. Other expression vectors for use in mammalian host cells can be constructed as disclosed by Okayama and Berg, *Mol. Cell. Biol.* (1983) 3:280. A useful system for stable high level expression of mammalian cDNAs in C127 murine mammary epithelial cells can be constructed substantially as described by Cosman et al., *Mol. Immunol.* (1986) 23:935. A useful high expression vector, PMLSV N1/N4, described by Cosman et al., *Nature* (1984) 312:768, has been deposited as ATCC 39890. Additional useful mammalian expression vectors are described in EP0367566, and in WO91/18982, incorporated by reference herein. In yet another alternative, the vectors can be derived from retroviruses.

Another useful expression vector, pFLAG®, can be used. FLAG® technology is centered on the fusion of a low molecular weight (1 kD), hydrophilic, FLAG® marker peptide to the N-terminus of a recombinant protein expressed by pFLAG® expression vectors.

Regarding signal peptides that can be employed, the native signal peptide can be replaced by a heterologous signal peptide or leader sequence, if desired. The choice of signal peptide or leader can depend on factors such as the type of host cells in which the recombinant polypeptide is to be produced. To illustrate, examples of heterologous signal peptides that are functional in mammalian host cells include the signal sequence for interleukin-7 (IL-7) described in U.S. Pat. No. 4,965,195; the signal sequence for interleukin-2 receptor described in Cosman et al., *Nature* (1984) 312:768; the interleukin-4 receptor signal peptide described in EP 367,566; the type I interleukin-1 receptor signal peptide described in U.S. Pat. No. 4,968,607; and the type II interleukin-1 receptor signal peptide described in EP 460,846.

The "isolated" polypeptides or fragments thereof encompassed by this invention are polypeptides or fragments that are not in an environment identical to an environment in which it or they can be found in nature. The "purified" polypeptides or fragments thereof encompassed by this invention are essentially free of association with other proteins or polypeptides, for example, as a purification product of recombinant expression systems such as those described above or as a purified product from a non-recombinant source such as naturally occurring cells and/or tissues.

With respect to any type of host cell, as is known to the skilled artisan, procedures for purifying a recombinant polypeptide or fragment will vary according to such factors as the type of host cells employed and whether or not the recombinant polypeptide or fragment is secreted into the culture medium.

In general, the recombinant polypeptide or fragment can be isolated from the host cells if not secreted, or from the medium or supernatant if soluble and secreted, followed by one or more concentration, salting-out, ion exchange, hydrophobic interaction, affinity purification or size exclusion chromatography steps. As to specific ways to accomplish these steps, the culture medium first can be concentrated using a commercially available protein concentration filter, for example, an Amicon or Millipore Pellicon ultrafiltration unit. Following the concentration step, the concentrate can be applied to a purification matrix such as a gel filtration medium. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. In addition, a chromatofocusing step can be employed. Alternatively, a hydrophobic interaction chromatography step can be employed. Suitable matrices can be phenyl or octyl moieties bound to resins. In addition, affinity chromatography with a matrix which selectively binds the recombinant protein can be employed. Examples of such resins employed are lectin columns, dye columns, and metal-chelating columns. Finally, one or more reverse-phase high performance liquid chromatography (RP-HPLC) steps employing hydrophobic RP-HPLC media, (e.g., silica gel or polymer resin having pendant methyl, octyl, octyldecyl or other aliphatic groups) can be employed to further purify the polypeptides. Some or all of the foregoing purification steps, in various combinations, are well known and can be employed to provide an isolated and purified recombinant protein.

It is also possible to utilize an affinity column comprising a polypeptide-binding protein of the invention, such as a monoclonal antibody generated against polypeptides of the invention, to affinity-purify expressed polypeptides. These polypeptides can be removed from an affinity column using conventional techniques, e.g., in a high salt elution buffer and then dialyzed into a lower salt buffer for use or by changing pH or other components depending on the affinity matrix utilized, or be competitively removed using the naturally occurring substrate of the affinity moiety, such as a polypeptide derived from the invention.

In this aspect of the invention, polypeptide-binding proteins, such as the anti-polypeptide antibodies of the invention or other proteins that may interact with the polypeptide of the invention, can be bound to a solid phase support such as a column chromatography matrix or a similar substrate suitable for identifying, separating, or purifying cells that express polypeptides of the invention on their surface. Adherence of polypeptide-binding proteins of the invention to a solid phase contacting surface can be accomplished by any means. For example, magnetic microspheres can be coated with these polypeptide-binding proteins and held in the incubation vessel through a magnetic field. Suspensions of cell mixtures are contacted with the solid phase that has such polypeptide-binding proteins thereon. Cells having polypeptides of the invention on their surface bind to the fixed polypeptide-binding protein and unbound cells then are washed away. This affinity-binding method is useful for purifying, screening, or separating such polypeptide-expressing cells from solution. Methods of releasing positively selected cells from the solid phase are known in the art and encompass, for example, the use of enzymes. Such enzymes are preferably non-toxic and non-injurious to the cells and are preferably directed to cleaving the cell-surface binding partner.

Alternatively, mixtures of cells suspected of containing polypeptide-expressing cells of the invention first are incubated with a biotinylated polypeptide-binding protein of the invention. Incubation periods are typically at least one hour in duration to ensure sufficient binding to polypeptides of the invention. The resulting mixture then is passed through a column packed with avidin-coated beads, whereby the high affinity of biotin for avidin provides the binding of the polypeptide-binding cells to the beads. Use of avidin-coated beads is known in the art. See Berenson, et al. *J. Cell. Biochem* (1986) 10D:239. Wash of unbound material and the release of the bound cells is performed using conventional methods.

The desired degree of purity depends on the intended use of the protein. A relatively high degree of purity is desired when the polypeptide is to be administered in vivo, for example. In such a case, the polypeptides are purified such that no protein bands corresponding to other proteins are detectable upon analysis by SDS-polyacrylamide gel electrophoresis (SDS-PAGE). It will be recognized by one skilled in the pertinent field that multiple bands corresponding to the polypeptide can be visualized by SDS-PAGE, due to differential glycosylation, differential post-translational processing, and the like. Most preferably, the polypeptide of the invention is purified to substantial homogeneity, as indicated by a single protein band upon analysis by SDS-PAGE. The protein band can be visualized by silver staining, Coomassie blue staining, or (if the protein is radiolabeled) by autoradiography.

The purified polypeptides of the invention (including proteins, polypeptides, fragments, variants, oligomers, and other forms) can be tested for the ability to bind the binding partner in any suitable assay, such as a conventional binding assay. The polypeptide can be labeled with a detectable reagent (e.g., a radionuclide, chromophore, enzyme that catalyzes a colorimetric or fluorometric reaction, and the like). The labeled polypeptide is contacted with cells expressing the binding partner. The cells then are washed to remove unbound labeled polypeptide, and the presence of cell-bound label is determined by a suitable technique, chosen according to the nature of the label.

Another type of competitive binding assay utilizes radiolabeled soluble binding partner, such as a soluble 4833427G06Rik/Fc fusion protein, and intact cells expressing a specific antibody. Qualitative results can be obtained by competitive autoradiographic plate binding assays, while Scatchard plots (Scatchard, *Ann. N.Y. Acad. Sci.* (1949) 51:660) may be utilized to generate quantitative results. Such binding assays can be useful in evaluating the biological activity of a variant polypeptide by assaying for the variant's ability to compete with the native protein for binding to the binding partner.

The 4833427G06Rik polypeptide of the present invention can also be used in a screening assay for compounds and small molecules which inhibit activation by (antagonize) the 4833427G06Rik polypeptide of the instant invention. Thus, polypeptides of the invention can be used to identify antagonists from, for example, cells, cell-free preparations, chemical libraries, and natural product mixtures. The antagonists can be natural or modified substrates, ligands, enzymes, or receptors of the 4833427G06Rik polypeptide, or can be structural or functional mimetics of the 4833427G06Rik polypeptide. The antagonists may further be small molecules, peptides, antibodies and antisense oligonucleotides.

One embodiment of a method for identifying compounds which antagonize the 4833427G06Rik polypeptide is contacting a candidate compound with cells which respond to 4833427G06Rik polypeptide and observe the binding of 4833427G06Rik to the cells, or stimulation or inhibition of a functional response. The activity of the cells which were contacted with the candidate compound could then be compared with the identical cells which were not contacted for 4833427G06Rik polypeptide activity and 4833427G06Rik polypeptide agonists and antagonists could be identified. A still further embodiment of the instant invention provides a method of identifying compounds that inhibit the synthesis or secretion of 4833427G06Rik by contacting the candidate compound with cells which express 4833427G06Rik polypeptide and measuring the 4833427G06Rik production. The measurement of 4833427G06Rik production could be performed by a number of well-known methods such as measuring the amount of protein present (for example, by ELISA) or of the protein's activity.

The purified polypeptides according to the invention will facilitate the discovery of inhibitors (or antagonists) and/or agonists of such polypeptides. The use of a purified polypeptide of the invention in the screening of potential inhibitors and/or agonists thereof is important and can eliminate or reduce the possibility of interfering reactions with contaminants.

In addition, polypeptides of the invention can be used for structure-based design of polypeptide-inhibitors and/or agonists. Such structure-based design is also known as "rational drug design." The polypeptides can be three-dimensionally analyzed by, for example, X-ray crystallography, nuclear magnetic resonance or homology modeling, all of which are well-known methods. The use of the polypeptide structural information in molecular modeling software systems to assist in inhibitor design and inhibitor-polypeptide interaction is also encompassed by the invention. Such computer-assisted modeling and drug design can utilize information such as chemical conformational analysis, electrostatic potential of the molecules, protein folding, etc. For example, most of the design of class-specific inhibitors of metalloproteases has focused on attempts to chelate or bind the catalytic zinc atom. Synthetic inhibitors are usually designed to contain a negatively-charged moiety to which is attached a series of other groups designed to fit the specificity pockets of the particular protease. A particular method of the invention comprises analyzing the three dimensional structure of polypeptides of the invention for likely binding sites of substrates, synthesizing a new molecule that incorporates a predictive reactive site, and assaying the new molecule as described above.

Specific screening methods are known in the art and along with integrated robotic systems and collections of chemical compounds/natural products are extensively incorporated in high throughput screening so that large numbers of test compounds can be tested for antagonist or agonist activity within a short amount of time. These methods include homogeneous assay formats such as fluorescence resonance energy transfer, fluorescence polarization, time-resolved fluorescence resonance energy transfer, scintillation proximity assays, reporter gene assays, fluorescence quenched enzyme substrate, chromogenic enzyme substrate and electrochemiluminescence, as well as more traditional heterogeneous assay formats such as enzyme-linked immunosorbant assays (ELISA) or radioimmunoassays. Homogeneous assays are preferred. Also comprehended herein are cell-based assays, for example those utilizing reporter genes, as well as functional assays that analyze the effect of an antagonist or agonist on biological function(s) or activity(ies) of 4833427G06Rik or its products.

Accordingly, in one aspect of the invention, there is provided a method for screening a test compound to determine whether the test compound affects (or modulates) a biological activity of an 4833427G06Rik gene product, the method comprising contacting the test compound and the 4833427G06Rik gene product with cells capable of exhibiting the biological activity when contacted with the 4833427G06Rik gene product, and analyzing the cells for the occurrence of the biological activity, wherein if the biological activity observed in the presence of the test compound differs from the biological activity that is observed when the test compound is absent, the test compound affects the biological activity of the 4833427G06Rik gene product. The cells can be contacted in vitro or in vivo. The 4833427G06Rik gene product can be expressed by the cell, either endogenously or from an expression vector.

4833427G06Rik mediated modulation of signaling pathways is believed to involve a cascade of molecular changes, for example wherein a receptor propagates a ligand-receptor mediated signal by specifically activating intracellular kinases which phosphorylate target substrates (which can themselves be kinases that become activated following phosphorylation, or adaptor molecules that facilitate down-stream signaling through protein-protein interaction following phosphorylation), resulting in the activation of other factors (for example, NFκB). When the screening methods of the present invention include assaying for 4833427G06Rik-induced modulation of signaling pathways, the signaling pathways that may be assayed include those involving activation of NFκB. Assaying for activation signaling cascades further includes detecting phosphorylation of molecules that occurs during the signaling cascade, as in the phosphorylation of IκB (including IκB degradation assays, and assays for free IκB), p38 MAP kinase, and Stress-Activated Protein Kinase (SAPK/JNK).

Moreover, those of skill in the art understand that biological activity(ies) is/are most often induced by the binding of a ligand (i.e., a 4833427G06Rik gene product) to a receptor (counter-structure or binding moiety) present on or in a cell; accordingly, as previously described, 4833427G06Rik gene products (including 4833427G06Rik polypeptide fragments) can be used in binding studies to identify receptor-expressing cells. Such binding studies also provide assays useful in the inventive methods. 4833427G06Rik polypeptides can also be used to clone receptors (or other molecules that bind 4833427G06Rik gene products) and to screen for molecules that block receptor/ligand interactions. Those of ordinary skill in the art further understand that biological activities include cell proliferation, cell death, and changes in cell morphology and/or function (for example, activation, maturation); assays that evaluate such effects of 4833427G06Rik are known in the art, and will also be useful in the inventive methods. Moreover, animal models of syndromes and/or conditions, such as those disclosed herein, are useful for screening compounds for biological activity, including screening for antagonism (or agonism) of 4833427G06Rik.

The inventive methods further encompass performing more than one assay to discover and/or analyze agonists or antagonists of 4833427G06Rik activity (i.e., combination methods). Generally, such methods comprise selecting test compounds that affect a property of 4833427G06Rik (i.e., an ability of 4833427G06Rik to bind a 4833427G06Rik counter structure), then testing the selected compounds for an effect on another property of 4833427G06Rik (i.e., contacting the selected test compounds and an 4833427G06Rik polypeptide with cells capable of exhibiting a biological activity when contacted with 4833427G06Rik, and determining whether the compounds affect the biological activity). For example, the inventive methods can comprise a first assay to determine whether a candidate molecule interacts with (binds to) 4833427G06Rik. In one embodiment, the first assay is in a high throughput format, numerous forms of which are known in the art and disclosed herein. Such an assay will generally comprise the steps of: contacting test compounds and an 4833427G06Rik polypeptide with an 4833427G06Rik counter-structure; determining whether the test compounds affect the ability of 4833427G06Rik to bind the counter-structure; and selecting one or more test compounds that affect the ability of 4833427G06Rik to bind the counter-structure. The inventive combination methods further comprise evaluating selected compounds in a second assay, for agonistic or antagonistic effect on biological activity using one or more of the aforementioned assays.

Alternatively, the inventive combination methods can comprise a first assay to determine whether a candidate molecule modulates a biological activity of 4833427G06Rik, as described herein using an in vitro assay or an in vivo assay (for example, an animal model). According to such combination methods, molecules that modulate an 4833427G06Rik biological activity in this manner are selected using one or more of the aforementioned assays for biological activity, and assayed to determine whether the candidate molecule(s) bind 4833427G06Rik. The selected molecules can be tested to further define the exact region or regions of 4833427G06Rik to which the test molecule binds (for example, epitope mapping for antibodies).

As disclosed previously, the types of assays for biological activities of 4833427G06Rik that can be used in the inventive combination methods include assays for the expression of cytokines, assays for the expression of cell-surface molecules, assays to detect activation of signaling molecules, assays to detect induction of mRNAs, and assays that evaluate cell proliferation or cell death (and combinations thereof), as described herein. Molecules that bind and that have an agonistic or antagonistic effect on biologic activity will be useful in treating or preventing diseases or conditions with which the polypeptide(s) are implicated.

Those of ordinary skill in the art understand that when the biological activity observed in the presence of the test compound is greater than that observed when the test compound is absent, the test compound is an agonist of 4833427G06Rik, whereas when the biological activity observed in the presence of the test compound is less than that observed when the test compound is absent, the test compound is an antagonist (or inhibitor) of 4833427G06Rik. Generally, an antagonist will decrease or inhibit, an activity by at least 30%; more preferably, antagonists will inhibit activity by at least 50%, most preferably by at least 90%. Similarly, an agonist will increase, or enhance, an activity by at least 20%; more preferably, agonists will enhance activity by at least 30%, most preferably by at least 50%. Those of skill in the art will also recognize that agonists and/or antagonists with different levels of agonism or antagonism respectively can be useful for different applications (i.e., for treatment of different disease states).

Homogeneous assays are mix-and-read style assays that are very amenable to robotic application, whereas heterogeneous assays require separation of free from bound analyte by more complex unit operations such as filtration, centrifugation or washing. These assays are utilized to detect a wide variety of specific biomolecular interactions (including protein-protein, receptor-ligand, enzyme-substrate, and so on), and the inhibition thereof by small organic molecules. These assay methods and techniques are well known in the art (see, e.g., "High Throughput Screening: The Discovery of Bioactive Substances", John P. Devlin (ed.), Marcel Dekker, New York, 1997 ISBN: 0-8247-0067-8). The screening assays of the present invention are amenable to high throughput screening of chemical libraries and are suitable for the identification of small molecule drug candidates, antibodies, peptides, and other antagonists and/or agonists, natural or synthetic. Several useful assays are disclosed in US 2003-0165985 (the relevant disclosure of which is hereby incorporated by reference).

The methods of the invention can be used to identify antagonists (also referred to as inhibitors) and agonists of 4833427G06Rik activity from cells, cell-free preparations, chemical libraries, cDNA libraries, recombinant antibody libraries (or libraries comprising subunits of antibodies) and natural product mixtures. The antagonists and agonists can be natural or modified substrates, ligands, enzymes, receptors, etc. of the polypeptides of the instant invention, or can be structural or functional mimetics of 4833427G06Rik or its binding partner/counter-structure. Potential antagonists of the instant invention include small molecules, peptides and antibodies that bind to and occupy a binding site of the inventive polypeptides or a binding partner thereof, causing them to be unavailable to bind to their natural binding partners and therefore preventing normal biological activity. Antagonists also include chemicals (including small molecules and peptides) that interfere with the signaling pathways used by 4833427G06Rik (for example, by inhibiting the interaction of receptor subunits, or inhibiting the interaction of intracellular components of the signaling cascade). Potential agonists include small molecules, peptides and antibodies which bind to the instant polypeptides or binding partners thereof, and elicit the same or enhanced biologic effects as those caused by the binding of the polypeptides of the instant invention. Moreover, substances that activate (or enhance) the signaling pathways used by 4833427G06Rik are also included within the scope of agonists of 4833427G06Rik.

Small molecule agonists and antagonists are usually less than 10K molecular weight and can possess a number of physicochemical and pharmacological properties which enhance cell penetration, resist degradation and prolong their physiological half-lives. Antibodies, which include intact molecules as well as fragments such as Fab and F(ab')2 fragments, as well as recombinant molecules derived therefrom (including antibodies expressed on phage, intrabodies, single chain antibodies such as scFv and other molecules derived from immunoglobulins that are known in the art), can be used to bind to and inhibit the polypeptides of the instant invention by blocking the propagation of a signaling cascade. It is preferable that the antibodies are humanized, and more preferable that the antibodies are human. The antibodies of the present invention can be prepared by any of a variety of well-known methods, as disclosed herein.

Additional examples of candidate molecules, also referred to herein as "test molecules" or "test compounds," to be tested for the ability to modulate 4833427G06Rik activity include, but are not limited to, carbohydrates, small molecules (usually organic molecules or peptides), proteins, and nucleic acid molecules (including oligonucleotide fragments typically consisting of from 8 to 30 nucleic acid residues). Peptides to be tested typically consist of from 5 to 25 amino acid residues. Also, candidate nucleic acid molecules can be antisense nucleic acid sequences, and/or can possess ribozyme activity.

The methods of the invention can be used to screen for antisense molecules that inhibit the functional expression of one or more mRNA molecules that encode one or more proteins that mediate an 4833427G06Rik-dependent cellular response. An antisense nucleic acid molecule is a DNA sequence that is capable of can hybridizing to the target mRNA molecule through Watson-Crick base pairing, and inhibiting translation thereof. Alternatively, the DNA can be inverted relative to its normal orientation for transcription and so express an RNA transcript that is complementary to the target mRNA molecule (i.e., the RNA transcript of the antisense nucleic acid molecule can hybridize to the target mRNA molecule through Watson-Crick base pairing). An anti-sense nucleic acid molecule can be constructed in a number of different ways provided that it is capable of interfering with the expression of a target protein. Typical anti-sense oligonucleotides to be screened preferably are 30-40 nucleotides in length. The anti-sense nucleic acid molecule generally will be substantially identical (although in antisense orientation) to the target gene. The minimal identity will typically be greater than about 80%, but a higher identity might exert a more effective repression of expression of the endogenous sequences. Substantially greater identity of more than about 90% is preferred, though about 95% to absolute identity would be most preferred.

Candidate nucleic acid molecules can possess ribozyme activity. Thus, the methods of the invention can be used to screen for ribozyme molecules that inhibit the functional expression of one or more mRNA molecules that encode one or more proteins that mediate an IL-1β dependent cellular response. Ribozymes are catalytic RNA molecules that can cleave nucleic acid molecules having a sequence that is completely or partially homologous to the sequence of the ribozyme. It is possible to design ribozyme transgenes that encode RNA ribozymes that specifically pair with a target RNA and cleave the phosphodiester backbone at a specific location, thereby functionally inactivating the target RNA. In carrying out this cleavage, the ribozyme is not itself altered, and is thus capable of recycling and cleaving other molecules. The inclusion of ribozyme sequences within antisense RNAs confers RNA-cleaving activity upon them, thereby increasing the activity of the antisense constructs.

The design and use of target RNA-specific ribozymes is described in Haseloff et al., *Nature* (1988) 334:585, and U.S. Pat. No. 5,646,023, both of which publications are incorporated herein by reference. Tabler et al., *Gene* (1991) 108:175 have greatly simplified the construction of catalytic RNAs by combining the advantages of the anti-sense RNA and the ribozyme technologies in a single construct. Smaller regions of homology are required for ribozyme catalysis, therefore this can promote the repression of different members of a large gene family if the cleavage sites are conserved.

Among the uses of polynucleotides of the invention is the use of fragments as probes or primers. Such fragments generally comprise at least about 17 contiguous nucleotides of a DNA sequence. In other embodiments, a DNA fragment comprises at least 30, or at least 60, contiguous nucleotides of a DNA sequence.

Because homologs of 4833427G06Rik from other mammalian species are contemplated herein, probes based on the mouse DNA sequence of 4833427G06Rik can be used to screen cDNA libraries derived from other mammalian species, using conventional cross-species hybridization techniques. Using knowledge of the genetic code in combination with the amino acid sequences set forth above, sets of degenerate oligonucleotides can be prepared. Such oligonucleotides are useful as primers, e.g., in polymerase chain reactions (PCR), whereby DNA fragments are isolated and amplified.

DNA of the present invention can be used in developing treatments for any disorder mediated (directly or indirectly) by defective, or insufficient amounts of, the genes corresponding to the polynucleotides of the invention. Disclosure herein of native nucleotide sequences permits the detection of defective genes, and the replacement thereof with normal genes. Defective genes can be detected in in vitro diagnostic assays, and by comparison of a native nucleotide sequence disclosed herein with that of a gene derived from a person suspected of harboring a defect in this gene.

Other useful fragments of the polynucleotides of this invention include antisense or sense oligonucleotides comprising a single-stranded polynucleotide sequence (either RNA or DNA) capable of binding to target mRNA (sense) or DNA (antisense) sequences. Anti-sense or sense oligonucleotides according to the present invention comprise a fragment of DNA (SEQ ID NO:5). Such a fragment generally comprises at least about 14 nucleotides, for example from about 14 to about 30 nucleotides. The ability to derive an antisense or a sense oligonucleotide, based upon a cDNA sequence encoding a given protein is described in, for example, Stein and Cohen, *Cancer Res.* (1988) 48:2659 and van der Krol et al., *BioTechniques* (1988) 6:958.

Binding antisense or sense oligonucleotides to target polynucleotide sequences results in the formation of duplexes that block or inhibit protein expression by one of several means, including enhanced degradation of the mRNA by RNAseH, inhibition of splicing, premature termination of transcription or translation, or by other means. The antisense oligonucleotides thus can be used to block expression of proteins. Antisense or sense oligonucleotides further comprise oligonucleotides having modified sugar-phosphodiester backbones (or other sugar linkages, such as those described in WO91/06629) and wherein such sugar linkages are resistant to endogenous nucleases. Such oligonucleotides with resistant sugar linkages are stable in vivo (i.e., capable of resisting enzymatic degradation) but retain sequence specificity to be able to bind to target nucleotide sequences.

Other examples of sense or antisense oligonucleotides include those oligonucleotides which are covalently linked to organic moieties, such as those described in WO 90/10448, and other moieties that increases affinity of the oligonucleotide for a target polynucleotide sequence, such as poly-(L-lysine). Further still, intercalating agents, such as ellipticine, and alkylating agents or metal complexes can be attached to sense or antisense oligonucleotides to modify binding specificities of the antisense or sense oligonucleotide for the target nucleotide sequence.

Antisense or sense oligonucleotides can be introduced into a cell containing the target polynucleotide sequence by any gene transfer method, including, for example, lipofection, $CaPO_4$-mediated DNA transfection, electroporation, or by using gene transfer vectors such as Epstein-Barr virus.

Sense or antisense oligonucleotides also can be introduced into a cell containing the target nucleotide sequence by formation of a conjugate with a ligand binding molecule, as described in WO 91/04753. Suitable ligand binding molecules include, but are not limited to, cell surface receptors, growth factors, other cytokines, or other ligands that bind to cell surface receptors. Preferably, conjugation of the ligand binding molecule does not substantially interfere with the ability of the ligand binding molecule to bind to its corresponding molecule or receptor, or block entry of the sense or antisense oligonucleotide or its conjugated version into the cell.

Alternatively, a sense or an antisense oligonucleotide can be introduced into a cell containing the target polynucleotide sequence by formation of an oligonucleotide-lipid complex, as described in WO 90/10448. The sense or antisense oligonucleotide-lipid complex is preferably dissociated within the cell by an endogenous lipase.

Polypeptides of the present invention find use as a protein purification reagent. The polypeptides can be attached to a solid support material and used to purify the binding partner proteins by affinity chromatography. In particular embodiments, a polypeptide (in any form described herein that is capable of binding the binding partner) is attached to a solid support by conventional procedures. As one example, chromatography columns containing functional groups that will react with functional groups on amino acid side chains of proteins are available (Pharmacia Biotech, Inc., Piscataway, N.J.). In an alternative, a polypeptide/Fc protein (as discussed above) is attached to Protein A- or Protein G-containing chromatography columns through interaction with the Fc moiety.

The polypeptide also finds use in purifying or identifying cells that express the binding partner on the cell surface. Polypeptides are bound to a solid phase such as a column chromatography matrix or a similar suitable substrate. For example, magnetic microspheres can be coated with the polypeptides and held in an incubation vessel through a magnetic field. Suspensions of cell mixtures containing the binding partner expressing cells are contacted with the solid phase having the polypeptides thereon. Cells expressing the binding partner on the cell surface bind to the fixed polypeptides, and unbound cells then are washed away. Alternatively, the polypeptides can be conjugated to a detectable moiety, then incubated with cells to be tested for binding partner expression. After incubation, unbound labeled matter is removed and the presence or absence of the detectable moiety on the cells is determined.

In a further alternative, mixtures of cells suspected of containing cells expressing the binding partner are incubated with biotinylated polypeptides. Incubation periods are typically at least one hour in duration to ensure sufficient binding. The resulting mixture then is passed through a column packed with avidin-coated beads, whereby the high affinity of biotin for avidin provides binding of the desired cells to the beads. Procedures for using avidin-coated beads are known (see Berenson, et al. *J Cell Biochem.* (1986) 10D:239). Washing to remove unbound material, and the release of the bound cells, are performed using conventional methods.

Polypeptides also find use in measuring the biological activity of the binding partner protein in terms of their binding affinity. The polypeptides thus can be employed by those conducting "quality assurance" studies, e.g., to monitor shelf life and stability of protein under different conditions. For example, the polypeptides can be employed in a binding affinity study to measure the biological activity of a binding partner protein that has been stored at different temperatures, or produced in different cell types. The proteins also can be used to determine whether biological activity is retained after modification of a binding partner protein (e.g., chemical modification, truncation, mutation, etc.). The binding affinity of the modified binding partner protein is compared to that of an unmodified binding partner protein to detect any adverse impact of the modifications on biological activity of the binding partner. The biological activity of a binding partner protein thus can be ascertained before it is used in a research study, for example.

Detectable (diagnostic) and therapeutic agents that can be attached to a polypeptide include, but are not limited to, toxins, other cytotoxic agents, drugs, radionuclides, chromophores, enzymes that catalyze a calorimetric or fluorometric reaction, and the like, with the particular agent being chosen according to the intended application. Among the toxins are ricin, abrin, diphtheria toxin, *Pseudomonas aeruginosa* exotoxin A, ribosomal inactivating proteins, mycotoxins such as trichothecenes, and derivatives and fragments (e.g., single chains) thereof. Radionuclides suitable for diagnostic use include, but are not limited to, $^{123}$I, $^{131}$I, $^{99m}$Tc, $^{111}$In, and $^{76}$Br. Examples of radionuclides suitable for therapeutic use are $^{131}$I, $^{211}$At, $^{77}$Br, $^{186}$Re, $^{188}$Re, $^{212}$Pb, $^{212}$Bi, $^{109}$Pd, $^{64}$Cu, and $^{67}$Cu.

Such agents can be attached to the polypeptide by any suitable conventional procedure. The polypeptide comprises functional groups on amino acid side chains that can be reacted with functional groups on a desired agent to form covalent bonds, for example. Alternatively, the protein or agent can be derivatized to generate or attach a desired reactive functional group. The derivatization can involve attachment of one of the bifunctional coupling reagents available for attaching various molecules to proteins (Pierce Chemical Company, Rockford, Ill.). A number of techniques for radiolabeling proteins are known. Radionuclide metals can be attached to polypeptides by using a suitable bifunctional chelating agent, for example.

Conjugates comprising polypeptides and a suitable diagnostic or therapeutic agent (preferably covalently linked) are thus prepared. The conjugates are administered or otherwise employed in an amount appropriate for the particular application.

Polypeptides of the invention can be used in developing treatments for any disorder mediated (directly or indirectly) by defective, or insufficient amounts of the polypeptides. Further, the polypeptides of the invention can be used in developing treatments for any disorder resulting (directly or indirectly) from an excess of the polypeptide. The polypeptides of the instant invention can be administered to a mammal afflicted with such disorders.

The polypeptides can also be employed in inhibiting a biological activity of the binding partner, in in vitro or in vivo procedures. For example, a purified Dog1 polypeptide can be used to inhibit binding of the endogenous Dog 1 gene product to its cellular receptor.

Polypeptides of the invention can be administered to a mammal to treat a binding partner-mediated disorder. Such binding partner-mediated disorders include conditions caused (directly or indirectly) or exacerbated by the binding partner.

Compositions of the present invention can contain a polypeptide in any form described herein, such as native proteins, variants, derivatives, oligomers, and biologically active fragments. In particular embodiments, the composition comprises a soluble polypeptide or an oligomer comprising soluble polypeptides of the invention.

Compositions comprising an effective amount of a polypeptide of the present invention, in combination with other components such as a physiologically acceptable diluent, carrier, or excipient, are provided herein. The polypeptides can be formulated according to known methods used to prepare pharmaceutically useful compositions. They can be combined in admixture, either as the sole active material or with other known active materials suitable for a given indication, with pharmaceutically acceptable diluents (e.g., saline, Tris-HCl, acetate, and phosphate buffered solutions), preservatives (e.g., thimerosal, benzyl alcohol, parabens), emulsifiers, solubilizers, adjuvants and/or carriers. Suitable formulations for pharmaceutical compositions include those described in "Remington's Pharmaceutical Sciences", 16th ed. 1980, Mack Publishing Company, Easton, Pa.

In addition, such compositions can be complexed with polyethylene glycol (PEG), metal ions, or incorporated into polymeric compounds such as polyacetic acid, polyglycolic acid, hydrogels, dextran, and the like, or incorporated into liposomes, microemulsions, micelles, unilamellar or multilamellar vesicles, erythrocyte ghosts or spheroblasts. Such compositions will influence the physical state, solubility, stability, rate of in vivo release, and rate of in vivo clearance, and are thus chosen according to the intended application.

The compositions of the invention can be administered in any suitable manner, e.g., topically, parenterally, or by inhalation. The term "parenteral" includes injection, e.g., by subcutaneous, intravenous, or intramuscular routes, also including localized administration, e.g., at a site of disease or injury. Those of ordinary skill in the art recognize that other types of localized administration (e.g., intraarticular, intracapsular, intracarpal, intracelial, intracerebroventricular, intrasynovial, intraspinal, intraligamentus, intrameningeal, intraocular, epidural, transepithelially, and/or administration by one or more of these routes at a site near or adjacent to a site of disease or injury) are suitable for use in administering the compositions of the present invention. Sustained release from implants is also contemplated.

One skilled in the pertinent art will recognize that suitable dosages will vary, depending upon such factors as the nature of the disorder to be treated, the patient's body weight, age, and general condition, and the route of administration. Preliminary doses can be determined according to animal tests, and the scaling of dosages for human administration is performed according to art-accepted practices.

Compositions comprising polynucleotides in physiologically acceptable formulations are also contemplated. DNA can be formulated for injection, for example. Moreover, inasmuch as those of ordinary skill in the art are aware that nucleic acid compositions (including DNA) are taken up by cells and result in the expression of protein in or near the area where the nucleic acid composition was administered, the inventive nucleic acid compositions will be useful for localized administration of polypeptides encoded thereby.

Another use of the polypeptide of the present invention is as a research tool for studying the biological effects that result from the interactions of a Dog1 gene product with its binding partner, or from inhibiting these interactions, on different cell types. Polypeptides also can be employed in in vitro assays for detecting 4833427G06Rik, the binding partner or the interaction thereof. The inventive polypeptides will also be useful in elucidating the signaling pathways of p53 family members, and in identifying molecules that modulate various aspects of such signaling pathways. The modulators identified by studies utilizing the inventive polypeptides have utility in treating or ameliorating a wide variety of diseases and syndromes in which cell cycle regulation or apoptosis plays a role.

Antibodies that are immunoreactive with the polypeptides of the invention are provided herein. Such antibodies specifically bind to the polypeptides via the antigen-binding sites of the antibody (as opposed to non-specific binding). Thus, the polypeptides, fragments, variants, fusion proteins, etc., as set forth above can be employed as "immunogens" in producing antibodies immunoreactive therewith. More specifically, the polypeptides, fragment, variants, fusion proteins, etc. contain antigenic determinants or epitopes that elicit the formation of antibodies.

These antigenic determinants or epitopes can be either linear or conformational (discontinuous). Linear epitopes are composed of a single section of amino acids of the polypeptide, while conformational or discontinuous epitopes are composed of amino acids sections from different regions of the polypeptide chain that are brought into close proximity upon protein folding (C. A. Janeway et al., "Immuno Biology" (1996) 3:9 (Garland Pub. Inc., 2nd ed.)). Because folded proteins have complex surfaces, the number of epitopes available is quite numerous; however, due to the conformation of the protein and steric hinderances, the number of antibodies that actually bind to the epitopes is less than the number of available epitopes (C. A. Janeway et al., "Immuno Biology" 2:14 (Garland Pub. Inc., 2nd ed. 1996)). Epitopes can be identified by any of the methods known in the art.

Thus, one aspect of the present invention relates to the antigenic epitopes of the polypeptides of the invention. Such epitopes are useful for raising antibodies, in particular monoclonal antibodies, as described in more detail below. Additionally, epitopes from the polypeptides of the invention can be used as research reagents, in assays, and to purify specific binding antibodies from substances such as polyclonal sera or supernatants from cultured hybridomas. Such epitopes or variants thereof can be produced using techniques well known in the art such as solid-phase synthesis, chemical or enzymatic cleavage of a polypeptide, or using recombinant DNA technology.

As to the antibodies that can be elicited by the epitopes of the polypeptides of the invention, whether the epitopes have been isolated or remain part of the polypeptides, both polyclonal and monoclonal antibodies can be prepared by conventional techniques. See, for example, Monoclonal Antibodies, Hybridomas: A New Dimension in Biological Analyses, Kennet et al. (eds.), Plenum Press, New York (1980); and Antibodies: A Laboratory Manual, Harlow and Land (eds.), Cold Spring Harbor Laboratory Press, Cold Spring Harbor, N.Y., (1988).

Hybridoma cell lines that produce monoclonal antibodies specific for the polypeptides of the invention are also contemplated herein. Such hybridomas can be produced and identified by conventional techniques. One method for producing such a hybridoma cell line comprises immunizing an animal with a polypeptide; harvesting spleen cells from the immunized animal; fusing said spleen cells to a myeloma cell line, thereby generating hybridoma cells; and identifying a hybridoma cell line that produces a monoclonal antibody that binds the polypeptide. The monoclonal antibodies can be recovered by conventional techniques.

The monoclonal antibodies of the present invention include chimeric antibodies, e.g., humanized versions of murine monoclonal antibodies. Such humanized antibodies can be prepared by known techniques and offer the advantage of reduced immunogenicity when the antibodies are administered to humans. In one embodiment, a humanized monoclonal antibody comprises the variable region of a murine antibody (or just the antigen binding site thereof) and a constant region derived from a human antibody. Alternatively, a humanized antibody fragment can comprise the antigen binding site of a murine monoclonal antibody and a variable region fragment (lacking the antigen-binding site) derived from a human antibody. Procedures for the production of chimeric and further engineered monoclonal antibodies include those described in Riechmann et al., *Nature* (1988) 332:323, Liu et al. (*Proc Natl Acad Sci USA* (1987) 84:3439, Larrick et al., *Bio/Technology* (1989) 7:934, and Winter and Harris (TIPS 14:139, May, 1993). Procedures to generate antibodies transgenically can be found in GB 2,272,440, U.S. Pat. No. 5,569,825 and U.S. Pat. No. 5,545,806 and related patents claiming priority therefrom, all of which are incorporated by reference herein.

Antigen-binding fragments of the antibodies, which can be produced by conventional techniques, are also encompassed by the present invention. Examples of such fragments include, but are not limited to, Fab and F(ab')$_2$ fragments. Antibody fragments and derivatives produced by genetic engineering techniques are also provided.

In one embodiment, the antibodies are specific for the polypeptides of the present invention and do not cross-react with other proteins. Screening procedures by which such antibodies can be identified are well known, and can involve immunoaffinity chromatography, for example.

The antibodies of the invention can be used in assays to detect the presence of the polypeptides or fragments of the invention, either in vitro or in vivo. The antibodies also can be employed in purifying polypeptides or fragments of the invention by immunoaffinity chromatography.

Those antibodies that additionally can block binding of the polypeptides of the invention to the binding partner can be used to inhibit a biological activity that results from such binding. Such blocking antibodies can be identified using any suitable assay procedure, such as by testing antibodies for the ability to inhibit binding of a Dog1 gene product to certain cells expressing the 4833427G06Rik receptors. Alternatively, blocking antibodies can be identified in assays for the ability to inhibit a biological effect that results from polypeptides of the invention binding to their binding partners to target cells. Antibodies can be assayed for the ability to inhibit 4833427G06Rik, or binding partner-mediated cell lysis, for example.

Such an antibody can be employed in an in vitro procedure, or administered in vivo to inhibit a biological activity mediated by the entity that generated the antibody. Disorders caused or exacerbated (directly or indirectly) by the interaction of the polypeptides of the invention with the binding partner thus can be treated. A therapeutic method involves in vivo administration of a blocking antibody to a mammal in an amount effective in inhibiting a binding partner-mediated biological activity. Monoclonal antibodies are generally preferred for use in such therapeutic methods. In one embodiment, an antigen-binding antibody fragment is employed.

Antibodies can be screened for agonistic (i.e., ligand-mimicking) properties. Such antibodies, upon binding to cell surface receptor, induce biological effects (e.g., transduction of biological signals) similar to the biological effects induced when IL-1 binds to cell surface IL-1 receptors. Agonistic antibodies can be used to activate vascular endothelial cells and lymphocytes, induce local tissue destruction and fever (Janeway et al., 1996, supra), stimulate macrophages and vascular endothelial cells to produce IL-6, and up-regulate molecules on the surface of vascular endothelial cells.

Compositions comprising an antibody that is directed against polypeptides of the invention, and a physiologically acceptable diluent, excipient, or carrier, are provided herein. Suitable components of such compositions are as described above for compositions containing polypeptides of the invention.

Also provided herein are conjugates comprising a detectable (e.g., diagnostic) or therapeutic agent, attached to the antibody. Examples of such agents are presented above. The conjugates find use in in vitro or in vivo procedures.

The present invention also encompasses transgenic animals with altered indicator gene activity. Recombinant clones derived from the genomic sequences, e.g., containing introns, will be useful for transgenic and knockout studies, including transgenic cells, organisms, and knockout animals, and for gene therapy. (See, e.g., Goodnow (1992) "Transgenic Animals" in Roitt (ed.) Encyclopedia of Immunology, Academic Press, San Diego, Calif., pp. 1502-1504; Travis, *Science* (1992) 254:707-10; Capecchi, *Science* (1989) 244:1288-92; Robertson (ed.) (1987) "Teratocarcinomas and Embryonic Stem Cells: A Practical Approach", IRL Press, Oxford; Rosenberg, *J. Clinical Oncology* (1992) 10:180-99; Hogan, et al. (eds.) (1994) "Manipulating the Mouse Embryo: A Laboratory Manual", 2nd edition, Cold Spring Harbor Press, NY; Wei, *Ann. Rev. Pharmacol. Toxicol.* (1997) 37:119-41; and Rajewsky, et al., *J. Clin. Inves.* (1996) 98:S51-S53.)

Examples of these techniques include: 1) Insertion of reporter genes operably linked to promoter regions from an indicator gene by microinjection, retroviral infection, or other means known to those skilled in the art, into appropriate fertilized embryos in order to produce a transgenic animal (see, e.g., Hogan, supra); and 2) homologous recombination (see, e.g., Capecchi, supra; and Zimmer and Gruss, *Nature* (1989) 338:150-53) into embryonic stem cells allowing for the introduction of mutant or normal, human or animal versions of genes into the germ line of an animal. The resulting knock-out animals can express the reporter gene in response to a stimulus that would otherwise induce transcription of the indicator gene, e.g., administration of a genotoxic compound.

The technique of homologous recombination is already known in the art. It substitutes an inserted gene for the native gene in the animal genome, and is thus useful for producing an animal that cannot express the original native gene but does express, for example, no receptor, an inserted mutant receptor, or an alternative form of the receptor. In the present invention, this technique results in an animal that produces a reporter gene product in response to stimulus with a genotoxic compound, instead of the native indicator gene products.

With respect to creation of transgenic animals, microinjection adds genes to the genome, but does not remove them, and so is useful for producing an animal which expresses its own and added proteins. One means available for producing a transgenic animal, for example a mouse, is as follows: Female mice are mated, and the resulting fertilized eggs are dissected from the oviducts. The eggs are stored in an appropriate medium such as M2 medium (see, e.g., Hogan, supra). DNA or cDNA encoding an indicator gene regulatory region or promoter operably linked to a reporter gene is purified from an appropriate vector by methods known in the art. Additional inducible promoters can be fused with the coding region of the DNA to provide an experimental means to regulate expression of the transgene. Alternatively, or in addition, additional tissue specific regulatory elements can be fused with the coding region to permit tissue-specific expression of the transgene. The DNA, in an appropriately buffered solution, is inserted into a microinjection needle, and the egg to be injected is put in a depression slide. The needle is inserted into the pronucleus of the egg, and the DNA solution is injected. The injected egg is then transferred into the oviduct of a pseudopregnant mouse (a mouse stimulated by the appropriate hormones to maintain pregnancy, but which is not actually pregnant), where it proceeds to the uterus, implants, and develops to term. As noted above, microinjection is not the only method for inserting DNA into the egg, and is used here only for exemplary purposes.

Transgenic animals of the invention can be used to screen or test compounds for genotoxicity, with the added advantage that one can simultaneously examine the effect of any metabolites of the compound that arise.

Utility

The methods and reagents of the invention are useful for determining the potential of a compound to cause genotoxicity upon administration to an animal. The methods of the invention can be practiced, for example, using available microarray technology, or by inserting reporter genes operably linked to heterologous or endogenous promoter sequences corresponding to or derived from the indicator genes. By administering test compounds to test cells in vitro, one can eliminate drug candidates exhibiting unacceptable genotoxicity without requiring expensive and time-consuming in vivo testing.

EXAMPLES

The following preparations and examples are given to enable those skilled in the art to more clearly understand and to practice the present invention. They should not be considered as limiting the scope of the invention, but merely as being illustrative and representative thereof.

Example 1

Phenotypic Assay

Drug formulation. All compounds were purchased from Sigma-Aldrich Fine Chemicals. The drugs were dissolved in DMSO, except for pyrene which was dissolved in MeOH. The concentration of each drug used for genotoxicity testing was based upon the concentration known to induce micronuclei formation in vitro. Where that concentration was not known, a wide range of drug concentrations ranging from 1 nM to 5 mM was tested. For both genotoxic and non-genotoxic agents, the highest concentration tested was determined by either cellular toxicity or compound solubility (Table 1).

Genotoxicity assay. C2C12 cells (ATCC) were grown in DMEM with 20% FBS, sodium pyruvate, pen-strep-glutamine, maintaining sub-confluent condition. The differentiation assay was performed according to the method described by P. L. Puri et al., *Nature Gen* (2002) 32:585-93, in growth media further containing 1% DMSO or compound in 1% DMSO final (see Table I for compounds and concentrations). The cells were incubated for 24 hours, washed with PBS and placed into differentiation media (DMEM, 2% horse serum, sodium pyruvate and Pen-strep-glutamine), without drug or vehicle. Cells were assayed visually for differentiation at 48 and 72 hours: differentiated cells form myotubes, while blocked or delayed cells maintain a monolayer with very few myotubes. If the block is extreme, the cells begin to die after 3 days in differentiation media (e.g. treatment with etoposide or cisplatin). Drugs were titrated for cytotoxicity by assessing the cell count after a 24 hour exposure to compound, relative to vehicle.

TABLE I

| Compound | ChemAbs ref. | Dose range (μg/ml) | Lowest effective dose (μg/ml) |
|---|---|---|---|
| DMSO | 67-68-5 | NA | NA |
| Famotidin | 76824-35-6 | 0.5-316[s] | NA |
| Pilocarpine HCl | 54-71-7 | 1.6-100[s] | NA |
| Cefoperazone (Na salt) | 62893-20-3 | 0.2-200[s] | NA |
| Clozapine | 5786-21-0 | 0.1-250[s] | NA |
| Clofibrate | 637-07-0 | 0.5-180[t] | NA |
| Benzylacetate | 140-11-4 | 0.5-50[t] | NA |
| Methylurea | 598-50-5 | 0.4-40[t] | NA |
| Phthalic acid diester | 117-87-7 | 0.1-100[s] | NA |
| Methanol | 67-56-1 | 1-12,206[t] | NA |
| Propafenone HCl | 54063-53-5 | 0.1-100[t] | NA |
| Mesalamine | 89-57-6 | 0.1-74[s] | NA |
| Timolol maleate | 26921-17-5 | 0.5-100[s] | NA |
| Tetracycline HCl | 64-75-5 | 0.1-50[s] | NA |
| Levamisole HCl | 16595-80-5 | 0.5-250[s] | NA |
| Terazosin HCl | 63590-64-7 | 0.5-500[t] | NA |
| Prostaglandin I$_2$ (Na salt) | 61849-14-7 | 0.5-55[t] | NA |
| Trichloroethylene | 79-01-6 | 0.7-254[s] | NA |
| Urethane | 51-79-6 | 0.03-35[t] | NA |
| Pyrene | 129-00-0 | 0.1-55[t] | NA |
| Methanesulfonate methyl ester (MMS) | 62-27-3 | 0.002-0.016[t] | 0.002 |
| Methanesulfonate ethyl ester (EMS) | 62-50-0 | 100-800[t] | 100 |
| 5-fluorouracil | 51-21-8 | 0.0008-0.0032[t] | 0.0008 |
| 2-nitrofluorene | 602-57-8 | 1.5-100[s] | 5.2 |
| 4-nitroquinoline N-oxide | 56-57-5 | 0.05-0.8[t] | 0.05 |
| 1-methyl-3-nitro-nitroso-guanidine (MNNG) | 70-25-7 | 0.1-0.8[t] | 0.1 |
| Diethylstilbestrol (DES) | 56-53-1 | 1.8-7.4[t] | 1.8 |
| Bleomycin sulfate | 9041-93-4 | 1-8[t] | 1 |
| Mitomycin C | 50-07-7 | 0.15-0.6[t] | 0.15 |
| Actinomycin D | 50-76-0 | 0.00075-0.003[t] | 0.00075 |
| Doxorubicin HCl | 25316-40-9 | 0.005-0.02[t] | 0.005 |
| Etoposide | 33419-42-0 | 0.25-2[t] | 0.5 |
| Cisplatin | 15663-27-1 | 0.15-0.8[t] | 0.15 |
| Vincristine sulfate | 206878-2 | 0.002-0.012[t] | 0.002 |
| Vinblastine sulfate | 143-67-9 | 0.0006-0.003[t] | 0.0006 |
| Amsacrine HCl | 54301-15-4 | 0.001-0.004[t] | 0.001 |
| Griseofulvin | 126-07-8 | 2-79[t] | 14 |
| Paclitaxel | 33069-62-4 | 0.002-1.4[t] | 0.002 |

[s]range limited by compound solubility
[t]range limited by compound toxicity

The genotoxic and non-genotoxic compounds were classified according to published results using the in vitro micronucleus formation test (W. von der Hude et al., *Mut Res* (2000) 468:137-63) or the chromosomal aberration test (S. Kalweit et al., *Mut Res* (1999) 439:183-90; B. Miller et al., *Mut Res* (1998) 410:81-116; B. Miller et al., *Mut Res* (1997) 392:45-59). The non-genotoxic compounds tested covered a wide range of chemical structures and therapeutic uses, including an anti-psychotic (clozapine), an anti-hyperlipoproteinemic (clofibrate), and an anesthetic (urethane) agent (Table 1). All 19 non-genotoxic agents, even when assayed over a wide range of concentrations, failed to block myogenic differentiation. In contrast, all 18 genotoxic drugs blocked C2C12 cell differentiation into myotubes at multiple concentrations tested. These compounds blocked differentiation at concentrations that did not cause detectable cellular cytotoxicity. The genotoxic compounds acted through a variety of different mechanisms, which included induction of breaks in double stranded DNA (bleomycin sulfate and etoposide), DNA alkylation (MMS and EMS), adduct formation (cisplatin and DES), DNA-intercalation (5-FU) and mitotic spindle formation inhibitors (Vincristine, Vinblastine and Paclitaxel). The results from this panel of compounds demonstrates that myocyte differentiation system can be used to identify genotoxic compounds.

Example 2

Genomic Assay

Gene expression analysis. After treatment with vehicle (DMSO) or compound (MMS—0.008 μg/ml; MNNG—4 μg/ml; cisplatin—0.6 μg/ml; etoposide—0.5 μg/ml; belomycin—0.5 μg/ml; vincristine sulfate—0.6 μg/ml) for 24 hours, C2C12 cells were washed to remove drug, changed to differentiation media to induce differentiation, and harvested at 6, 18 or 24 hours after induction. Three independent replicates were generated for each drug and time point. Sample processing was carried out according to protocols described in the Affymetrix Expression Analysis Technical Manual. Briefly, total RNA was isolated from cells by the acid guanidinium thiocyanate-phenol-chloroform extraction method (Trizol®, Invitrogen, Carlsbad, Calif.). Twice purified poly(A+) RNA was isolated and reverse transcribed using a T7-promoter coupled oligo(dT) primer, followed by in vitro transcription. The labeled samples were applied to the Affymetrix Murine Genome MOE430 set and were hybridized overnight at 45° C./60 rpm, washed using a FS450 Fluidics station, and scanned on a GS3000 scanner. The resulting image files were analyzed using Affymetrix software (Microarray Analysis Suite version 5.0).

To measure the effect of drug treatment on cellular gene expression, replicate data obtained from each drug and time point were compared with replicates for vehicle-matched controls using the Student t-test. The gene expression levels were Log transformed before applying the Student t-test. The fold change of the average expression level between the control and drug-treated cells was also calculated. A gene expression change after drug treatment was considered significant if all of the following conditions were satisfied for at least one gene and time point: First, the gene had to be expressed in either the drug-treated or vehicle-treated cells. A gene was considered expressed if the Affymetrix software determined that the gene was "present" in two out of the three replicates. This ensured that true expression changes were identified, and could be distinguished from background variability. Second, the calculated expression change for each of five tested drugs was at least 2 fold, and the calculated p-value for the expression change using the Student t-test was less than 0.01.

To further validate this experimental system, and to examine the mechanism by which these genotoxic agents inhibited myogenic differentiation, we used oligonucleotide microarrays to identify genes whose expression was altered in response to treatment with genotoxic drugs. Five of the profiled drugs were known to directly cause damage to cellular DNA. Vincristine sulfate causes genotoxicity by an indirect mechanism: it inhibits mitotic spindle formation by blocking tubulin polymerization. Consistent with having a different mechanism of action, vincristine induced a distinct pattern of gene expression changes relative to the five other drugs tested. Vinca alkaloids induced distinctly different changes in gene expression than did other tested drugs (see also U. Scherf et al., *Nature Gen* (2000) 24:236-44). Because of this, gene expression changes that were commonly induced after exposure to the five direct-acting genotoxic drugs were analyzed. Analysis of the gene expression data revealed that 86 genes had a significant change in the level of mRNA expression after treatment with the five direct-acting genotoxic drugs (the vincristine results were not used to select genes) (see Table 2). Each gene selected exhibited at least a 1.5-fold change in expression level after treatment with each of the five drugs, and the calculated p-value for each drug-induced expression change was less than 0.01. The expression of 28 genes was up-regulated after drug treatment, while that of 58 other genes was down-regulated.

TABLE 2

Fold change in expression in response to genotoxic compounds

| Symbol | Description | BLEO | CIS | ETOP | MMS | MNNG | VINC |
|---|---|---|---|---|---|---|---|
| Prelp | Proline arginine-rich end leucine-rich repeat | 0.23 | 0.12 | 0.34 | 0.19 | 0.11 | 0.58 |
| Sesn2 | Sestrin 2 | 4.20 | 3.80 | 4.20 | 5.30 | 5.80 | 2.38 |
| 4833427 G06 Rik | RIKEN cDNA | 5.40 | 3.70 | 11.30 | 3.70 | 4.00 | 0.98 |
| Dda3-pending | Differential display and activated by p53 | 5.00 | 3.30 | 4.50 | 3.70 | 3.80 | 2.00 |
| Usp30 | Ubiquitin specific protease 30 | 2.50 | 2.70 | | 3.70 | 2.60 | 2.00 |
| 0610013 D04 Rik | RIKEN cDNA | 2.80 | 2.60 | | 2.60 | 2.50 | 2.00 |
| Slc19a2 | Solute carrier family 19 (thiamine transporter), member 2 | 3.10 | 2.30 | 5.50 | 2.70 | 3.30 | 1.40 |
| Trp53-inp1 | Transformation related protein, 53 inducible nuclear protein 1 | 3.30 | 2.30 | 5.30 | 2.90 | 3.00 | 1.60 |
| D4Ertd-421e | DNA segment, Chr 4, ERATO Doi 421, expressed | 0.24 | 0.34 | | 0.44 | 0.40 | 0.64 |
| Shcbp1 | Shc SH2-domain binding protein 1 | 0.28 | 0.38 | 0.25 | 0.37 | 0.44 | 0.52 |
| Mki67 | Antigen identified by MAb Ki67 | 0.27 | 0.44 | 0.29 | 0.31 | 0.34 | 0.43 |
| Phex | Phosphate regulating neutral endopeptidase (X chromosome) | 2.40 | 2.50 | | 2.20 | 2.20 | 0.67 |
| Tk1 | Thymidine kinase 1 | 0.24 | 0.32 | 0.17 | 0.46 | 0.46 | 0.62 |
| Mmhead | *Mus musculus* 15 day embryo head cDNA clone | 2.50 | 2.10 | | 3.00 | 2.50 | 0.95 |
| Osbp16 | Oxysterol binding protein-like 6 | 2.10 | 2.10 | | 2.20 | 2.10 | 1.10 |
| M-phosph1 | M-phase phosphoprotein | 0.23 | 0.50 | 0.47 | 0.27 | 0.38 | 0.37 |
| Ephx1 | Epoxide hydrolase 1 (microsomal xenobiotic hydrolase) | 2.70 | 2.00 | 4.20 | 2.10 | 2.10 | 1.10 |
| Top2a | Topoisomerase (DNA) II alpha | 0.29 | 0.50 | 0.39 | 0.37 | 0.47 | 0.52 |
| Ccng1 | Cyclin G1 | 2.60 | 2.00 | 3.20 | 2.40 | 3.10 | 1.80 |
| Plf | Proliferin | 2.40 | 2.30 | | 2.60 | 2.00 | 1.10 |
| Np95 | Nuclear protein 95 | 0.31 | 0.47 | | 0.41 | 0.51 | 0.71 |
| Rad51-ap1 | RAD51-associated protein 1 | 0.32 | 0.50 | 0.36 | 0.45 | 0.52 | 0.59 |
| Nos3 | Nitric oxide synthase 3, endothelial cell | 2.60 | 2.00 | 5.20 | 1.90 | 2.10 | 1.30 |
| 2610005 B21 Rik | RIKEN cDNA | 0.25 | 0.39 | | 0.53 | 0.47 | 0.81 |
| Brca1 | Breast cancer 1 | 0.37 | 0.50 | 0.53 | 0.47 | 0.53 | 0.51 |
| Stk18 | Serine/threonine kinase 18 | 0.45 | 0.52 | 0.45 | 0.49 | 0.53 | 0.63 |
| Calm-bp1 | Calmodulin binding protein 1 | 0.28 | 0.54 | 0.43 | 0.30 | 0.41 | 0.40 |
| Lek1 | Leucine, glutamic acid, lysine family 1 protein | 0.30 | 0.54 | 0.46 | 0.36 | 0.36 | 0.45 |
| Smc2l1 | SMC2 structural maintenance of chromosomes 2-like 1 | 0.37 | 0.48 | 0.31 | 0.49 | 0.54 | 0.75 |
| E2f7 | E2F transcription factor 7 | 0.34 | 0.35 | 0.24 | 0.55 | 0.53 | 0.63 |
| Hmmr | Hyaluronan mediated motility receptor (RHAMM) | 0.26 | 0.55 | 0.53 | 0.36 | 0.47 | 0.52 |
| Nusap1 | Nucleolar and spindle associated protein 1 | 0.32 | 0.51 | 0.40 | 0.48 | 0.55 | 0.56 |
| Fbxo5 | f-box only protein 31 | 0.40 | 0.55 | 0.32 | 0.42 | 0.51 | 0.54 |
| Slc19a2 | Solute carrier family 19 | 2.50 | 1.80 | 4.30 | 2.30 | 2.20 | 1.10 |

TABLE 2-continued

Fold change in expression in response to genotoxic compounds

| Symbol | Description | BLEO | CIS | ETOP | MMS | MNNG | VINC |
|---|---|---|---|---|---|---|---|
| | (thiamine transporter), member 2 | | | | | | |
| 9030617O03Rik | RIKEN cDNA | 2.20 | 1.80 | 3.80 | 2.40 | 2.20 | 1.20 |
| Ly6e | Lymphocyte antigen 6 complex, locus E | 2.60 | 2.00 | 2.50 | 1.80 | 2.30 | 1.30 |
| 6530401L14Rik | RIKEN cDNA | 0.29 | 0.53 | 0.50 | 0.39 | 0.56 | 0.53 |
| Mad3 | Max dimerization protein 3 | 0.30 | 0.38 | | 0.52 | 0.56 | 0.89 |
| Hmgb2 | High mobility group box 2 | 0.31 | 0.46 | | 0.56 | 0.45 | 0.57 |
| Kif11 | Kinesin 11 | 0.30 | 0.57 | 0.31 | 0.43 | 0.53 | 0.46 |
| Mad2l1 | MAD2 (mitotic arrest deficient, homolog)-like 1 (yeast) | 0.30 | 0.57 | 0.40 | 0.43 | 0.55 | 0.64 |
| Asf1b | ASF1 anti-silencing function 1 homolog B (*Saccharomyces*) | 0.34 | 0.47 | 0.34 | 0.47 | 0.57 | 0.71 |
| Mcm3 | Minichromosome maintenance deficient 3 (*Saccharomyces*) | 0.41 | 0.48 | 0.40 | 0.56 | 0.57 | 0.69 |
| MGC:32192 | *Mus musculus* cDNA clone MGC: 32192 IMAGE: 5006129 | 0.27 | 0.40 | 0.32 | 0.46 | 0.58 | 0.71 |
| Foxm1 | Forkhead box M1 | 0.35 | 0.53 | 0.41 | 0.41 | 0.58 | 0.68 |
| Anxa8 | Annexin A8 | 2.60 | 1.70 | 5.60 | 2.50 | 2.80 | 1.80 |
| Slc35a5 | Solute carrier family 35, member A5 | 1.70 | 2.90 | | 2.60 | 2.50 | 1.30 |
| E030024M05Rik | RIKEN cDNA | 2.10 | 1.70 | 2.70 | 2.00 | 2.00 | 1.20 |
| Cks2 | CDC28 protein kinase regulatory subunit 2 | 0.34 | 0.41 | | 0.59 | 0.57 | 0.78 |
| Cilp | Cartilage intermediate layer pro | 0.59 | 0.38 | | 0.57 | 0.49 | 0.77 |
| Tacc3 | Transforming, acidic coiled-coil containing protein 3 | 0.43 | 0.42 | | 0.48 | 0.59 | 0.73 |
| Prc1 | Protein regulator of cytokinesis 1 | 0.45 | 0.58 | 0.42 | 0.44 | 0.59 | 0.63 |
| 2610509G12Rik | RIKEN cDNA | 0.49 | 0.50 | 0.46 | 0.55 | 0.59 | 0.55 |
| 2810417H13Rik | RIKEN cDNA | 0.25 | 0.36 | | 0.48 | 0.60 | 0.96 |
| Pbk | PDZ binding kinase | 0.27 | 0.45 | 0.26 | 0.46 | 0.60 | 0.62 |
| Capn6 | Calpain 6 | 0.57 | 0.56 | 0.36 | 0.60 | 0.60 | 0.83 |
| Gmnn | Geminin | 0.47 | 0.52 | 0.60 | 0.54 | 0.58 | 0.65 |
| Mcmd4 | Minichromosome maintenance deficient 4 homolog | 0.60 | 0.59 | 0.47 | 0.57 | 0.57 | 0.64 |
| Ccna2 | Cyclin A2 | 0.33 | 0.51 | 0.35 | 0.46 | 0.61 | 0.82 |
| Pola1 | DNA polymerase alpha 1, 180 kDa | 0.46 | 0.61 | 0.55 | 0.37 | 0.36 | 0.51 |
| Hmgb3 | High mobility group box 3 | 0.51 | 0.61 | 0.38 | 0.45 | 0.46 | 0.67 |
| Tagln | Transgelin (smooth muscle 22 protein) | 0.51 | 0.61 | | 0.47 | 0.55 | 0.84 |
| 1600013K19Rik | RIKEN cDNA | 0.48 | 0.60 | | 0.62 | 0.62 | 0.98 |
| Serpine1 | Ser (or Cys) proteinase inhibitor, clade E, member 1 | 0.54 | 0.54 | | 0.58 | 0.62 | 1.00 |
| Wig1 | Wild-type p53-induced gene 1 | 2.70 | 1.60 | 3.50 | 2.40 | 1.90 | 1.20 |
| Hgf | Hepatocyte growth factor (scatter factor) | 1.60 | 1.60 | 2.20 | 2.20 | 3.20 | 2.00 |
| Gnpi | Glucosamine-6-phosphate deaminase | 1.70 | 1.70 | | 1.60 | 1.90 | 1.60 |
| Birc5 | Baculoviral IAP repeat-containing 5 | 0.28 | 0.42 | | 0.51 | 0.63 | 0.87 |
| Prim1 | DNA primase, p49 subunit | 0.45 | 0.63 | 0.44 | 0.51 | 0.51 | 0.54 |
| Rbl1 | Retinoblastoma-like 1 (p107) | 0.48 | 0.58 | 0.38 | 0.59 | 0.64 | 0.67 |

TABLE 2-continued

| | | Fold change in expression in response to genotoxic compounds | | | | | |
|---|---|---|---|---|---|---|---|
| Symbol | Description | BLEO | CIS | ETOP | MMS | MNNG | VINC |
| Pcna | Proliferating cell nuclear antigen | 0.57 | 0.62 | 0.47 | 0.60 | 0.64 | 0.70 |
| E130315B21Rik | RIKEN cDNA | 0.58 | 0.56 | 0.55 | 0.64 | 0.60 | 0.70 |
| 2610019I03 RIK | RIKEN cDNA | 0.46 | 0.41 | | 0.43 | 065 | 0.76 |

Sixty of the 86 differentially expressed genes had a known annotated function in the Gene Ontology (www.geneontology.org/) index. The annotated functions of these genes indicated that the genotoxic drugs affected pathways relevant to cellular transformation and the DNA damage response. Of interest, p53 or c-Myc are known to regulate the transcription of 26 (58%) of these genes. The p53-regulated genes (2610509G12Rik, Birc5, Brca1, Calmbp1, Ccna2, Ccng1, Dda3, Hmgb2, Hmmr, Mcm3, Mcm4, Mki67, Nos3, Np95, Nusap1, Pcna, Pola1, Prc1, Rad51ap1, Slc19a2, Smc211, Tk1, Top2a, Trp53inp1, Wig1, Cks2, Lmnb1, Pbk) had been identified in published literature. The c-Myc regulated genes (Brca1, Ccna2, Ccng1, Cks2, Ephx1, Fabp5, Foxm1, Hmmr, Lmnb1, Mad211, Mcm3, Mcm4, Mcm5, Mki67, Pcna, Rad51ap1, Serpine1, Tk1, Ugt1a1) were identified using the Myc target gene database (www.myccancergene.org/index.asp). Furthermore, 32 of the 53 affected genes with functional annotation to a specific biological process were known to be involved in the response to DNA damage. In particular, 14 (26%) of these genes were annotated as being involved in DNA metabolism and 21 (40%) in cell cycle control. By comparison, only 3% and 5% of all annotated mouse genes are involved in DNA metabolism or cell cycle control.

The data demonstrate that a unique pattern of gene expression alteration occurs when cells that are not terminally differentiated are exposed to agents that directly damage DNA. This expression pattern (and subsets of the pattern) is thus useful for classifying other compounds and identifying compounds that are likely to cause direct DNA damage.

Example 3

RT-PCR Assay

An expression change in a subset of genes in this in vitro differentiation system could provide a universal indicator of DNA damage. Therefore, RT-PCR assays were developed for two genes whose expression was markedly increased after exposure to all of the direct-acting genotoxic agents. One was a novel gene of unknown function, Dog1 (4833427G06Rik). The other was Dda3, a gene whose expression has been shown to be both p53 and p73 responsive (P. K. Lo et al., Oncogene (1999) 18:7765-74), and which suppressed cell growth when over-expressed (S. C. Hsieh et al., Oncogene (2002) 21:3050-57). The RT-PCR assays were used to analyze mRNA prepared from C2C12 cell after exposure to 12 genotoxic (Actinomycin D (ACTD), diethylstilbestrol (DES), doxorubicin HCl (DOX), methane sulfonic acid ethyl ester (EMS), bleomycin sulfate (BLEO), cisplatin (CIS), etoposide (ETOP), methane sulfonic acid methyl ester (MMS), 1-methyl-3-nitro-nitrosoguanidine (MNG), vincristine sulfate (VINC), vinblastine sulfate (VINB), and paclitaxel (PACL)) and 9 non-genotoxic compounds (dimethyl sulfoxide (DMSO), cefoperazone sodium (CER), famotidin (FAM), pilocarpine HCl (PILO), timolol maleate (TIM), benzylacetate (BA), clofibrate (CLOF), mesalamine (MES), methylurea (MU), and phthalic acid diester (PTD)). After the cells were exposed to each drug for 24 hour, they were induced to differentiate for 18 hour before RNA was prepared.

Total RNA was Dnase1-treated and converted to cDNA using Multiscribe reverse transcriptase (Applied Biosystems Inc., Foster City, Calif.). The cDNA SYBR green real-time quantitative PCR assay was performed using the cDNA as template, and analyzed using an ABI PRISM 7900 Sequence Detector. The following primers and probes were designed for Dda3 and the novel Riken clone using Primer Express V. 2.0 software (Applied Biosystems Inc. Foster City, Calif.):

```
Dda3-139F
5'-GATCGGGTGCCTTGAGCTT-3';        (SEQ ID NO: 19)

Dda3-213R
5'-ACCTCTGCCCCTCTCTTCTTCT-3';     (SEQ ID NO: 20)

Dda-P-167T
5'-CAACCCCACCCTACCCTGCCCTG-3'     (SEQ ID NO: 21)

Rik-93F
5'-CAAATCAAAGGAAGTTTTATCAGAGTCA-3';(SEQ ID NO: 22)

Rik-182R
5'-GTCGATACCATATGTCAATCAAATCAT-3'; (SEQ ID NO: 23)

Rik-P-126T
5'-CCAAGGCTTTGACTTCTTCTTGGTCCCTT-  (SEQ ID NO: 24)
3'.
```

The expression of these two genes was significantly increased after exposure to each of the 12 genotoxic agents, but not after exposure to any of the 9 non-genotoxic drugs. The relative expression of 4833427G06Rik mRNA was increased by 2.3 to 13.9-fold after exposure to these genotoxic agents, and Dda3 was increased by 1.6 to 12.7 fold. The calculated p-value for the change in 4833427G06Rik mRNA expression after exposure to each drug relative to vehicle control was less than 0.001; and the p-values for the Dda3 mRNA expression change ranged from 0.04 (Paclitaxel) to 0.0001 (vinblastine). It was also important to determine if the change in expression of these two genes was relatively constant during the period after genotoxic compound exposure. To do this, the time course during which the expression of these two genes was elevated in differentiating C2C12 cells after exposure to genotoxic compounds was assessed. RT-PCR assays were performed on RNA samples obtained 6, 18 and 24 hours after induction of cellular differentiation after compound exposure. The expression of both genes was consistently elevated during the 6 to 24 hour period of differentiation induction after genotoxin exposure. It was surprising that vinblastine caused a much larger increase in expression of these indicator genes than did vincristine. Although vincristine and vinblastine are structurally similar Vinca alkaloids, and both act through inhibition of microtubule formation, they have a different clinical spectrum of activity (B. A. Chabner et al., "Goodman and Gilman's The Pharmacological Basis of Therapeutics" (J. G. Hardman and L. E. Limbard, Eds., McGraw-Hill, NH, 2001) chapter 52). Vincristine is used in treating pediatric leukemia and solid tumors, and is frequently used in adult lymphoma treatment. Vinblastine is used primarily of treating testicular carcinomas and lymphomas, and as second line therapy of various solid tumors.

To identify the Gene Ontology (GO) terms that were significantly enriched among the set of genes whose expression was affected by genotoxic drugs, we collected all of the annotated GO terms for each gene. For each term used in the GO annotation, the number of differentially expressed genes annotated with that term, or any subsidiary terms, was counted. The proportion of the differentially expressed genes with each GO annotation was compared with the proportion of the total number of mouse genes annotated with that GO term. This process enabled the GO terms that were enriched among the differentially expressed genes to be identified. Among the 53 genes with Genome Ontology annotation for biological processes, 32 were involved in the cellular response to DNA damage or regulation of the cell cycle.

Example 4

Inhibition of Dog1 with siRNA

The Dog1 mRNA encodes a predicted 18.7 KD protein with 165 amino acids. Analysis of the predicted amino acid sequence of murine Dog1 did not provide any information about its potential biologic function; no identifiable sequence motifs were identified. However, consistent with a potential role in the DNA damage response, there was a predicted bipartite nuclear localization signal in the amino acid sequence of the human homolog of Dog1. In addition, a highly conserved region near the carboxy terminus of the mouse and human genes was enriched in proline and basic amino acids (between positions 111 and 130 in the mouse protein). This extended charged segment can form a surface that can interact with other proteins or DNA. Since increased Dog1 expression strongly correlated with the response to DNA damage, we wanted to determine if this gene played role in the blockade of cellular differentiation after DNA damage. Therefore, we analyzed the effect of RNAi-mediated knockdown of Dog1 mRNA on C2C12 differentiation after mutagen-induced DNA damage. In these experiments, C2C12 cells were transfected with 3 different Dog1-specific siRNAs for 28 hours prior to exposure to a potent mutagen (75 µM MMS), and assessment of myogenic differentiation. Three different Dog1-specific siRNAs were used to ensure that the biologic effect was specifically caused by a decrease in the targeted gene. In addition, these siRNAs were designed using two different algorithms and obtained from two different companies. Analysis of Dog1 mRNA in these cells 28 hours after transfection revealed that each Dog1-specific siRNA reduced the amount of Dog1 mRNA by 80 to 96% relative to control. In contrast, control siRNAs did not significantly decrease Dog1 mRNA. C2C12 cell differentiation into myotubes was completely inhibited after genotoxin exposure. Neither mock transfection nor transfection with two different control siRNAs at 80 nM concentration could overcome the mutagen-induced blockade of C2C12 differentiation into myotubes. In contrast, transfection with each of the three Dog1-specific siRNAs at 20 nM enabled myocyte differentiation to proceed after mutagen exposure. Therefore, a specific reduction in Dog1 mRNA enabled C2C12 cells to undergo myogenic differentiation in the presence of damaged DNA.

The following siRNAs against Dog1 (4833427G06RIK) were designed using the SMARTPOOL (Dharmacon) or STEALTH (Invitrogen) algorithms; Dog1-2 is a pool of the following (SMARTPOOL) sequences:

```
Dog1-4;    GAAAGGAUCUCGAAAGAACUU;    (SEQ ID NO: 25)

Dog1-5;    GAAGAGAGAGCAAAGUAUCUU;    (SEQ ID NO: 26)

Dog1-6;    GCGGAACUCUAAAGUCGUUUU;    (SEQ ID NO: 27)
and

Dog1-7;    CAAAGGAAGUUUUAUCAGAUU.    (SEQ ID NO: 28)
```

The STEALTH sequences used were:

```
Dog1-1;    GGAUGCCAAUUUGGCUAAGCAGUUU;    (SEQ ID NO: 29)
and

Dog1-3;    CCUUUGAUCAGGACAAGGAUGCAAU.    (SEQ ID NO: 30)
```

Control siRNAs were obtained from Dharmacon:

Control-1; CCCUAUUCUCCUUCUUCGCUU (firefly luciferase control) (SEQ ID NO:31); and Control-2; a RISC-free proprietary sequence The four SMARTPOOL oligos were used as a pool (Dog 1-1). Control siRNAs, including the siCONTROL RISC-free RNA with a proprietary sequence and firefly luciferase control were obtained from Dharmacon. C2C12 cells were transfected in solution 24 with Optimem medium (Invitrogen) containing the siRNA at concentrations ranging from 10 to 80 nM for 5 hours and Lipofectamine 2000 (Invitrogen) at 2 µl lipid/well (12 well plate). The culture media was then changed to growth media without antibiotics. At 28 hours post-transfection, the culture media was changed to growth media plus antibiotics and vehicle or 75 µM MMS. After an additional 24 hours of incubation, the cells were washed, and the media was changed to differentiation media. The formation of myotubes was observed over the next 72 hours. The level of gene knockdown was quantitated by RT-PCR analysis at 28 hours post-transfection.

While the present invention has been described with reference to the specific embodiments thereof, it should be understood by those skilled in the art that various changes may be made and equivalents may be substituted without departing from the true spirit and scope of the invention. In addition, many modifications can be made to adapt a particular situation, material, composition of matter, process, process step or steps, to the objective spirit and scope of the present invention. All such modifications are intended to be within the scope of the claims appended hereto.

What is claimed:

1. A method for determining the genotoxicity of a test compound, said method comprising:
   (a) contacting a viable murine myoblast test cell with said test compound;
   (b) determining the change in expression level of a murine indicator gene selected from the group consisting of 4833427G06 Rik (RIKEN cDNA) (SEQ ID NO:5) and murine Dda3 (Differential display and activated by p53) wherein an increase in expression of at least 1.5-fold in said murine myoblast test cell, compared to a murine myoblast cell comprising 4833427G06 Rik (RIKEN cDNA) (SEQ ID NO: 5) or murine Dda3, that is not exposed to the test compound, indicates that said test compound exhibits genotoxicity.

2. The method of claim 1, wherein determining the change in expression level comprises measuring the amount of mRNA produced using RT-PCR.

3. The method of claim 1, wherein determining the change in expression level comprises measuring the increase in signal produced by increased expression of a label.

* * * * *